United States Patent
Thompson et al.

(10) Patent No.: US 9,210,928 B2
(45) Date of Patent: Dec. 15, 2015

(54) PLANT DEVELOPMENT CONTROL COMPOSITION

(75) Inventors: Andrew Thompson, Coventry (GB); Timothy Bugg, Coventry (GB)

(73) Assignee: Syngenta Crop Protection, LLC, Greensboro, NC (US)

(*) Notice: Subject to any disclaimer, the term of this patent is extended or adjusted under 35 U.S.C. 154(b) by 711 days.

(21) Appl. No.: 13/129,766

(22) PCT Filed: Nov. 17, 2009

(86) PCT No.: PCT/GB2009/002686
§ 371 (c)(1),
(2), (4) Date: Aug. 15, 2011

(87) PCT Pub. No.: WO2010/055316
PCT Pub. Date: May 20, 2010

(65) Prior Publication Data
US 2011/0301028 A1 Dec. 8, 2011

(30) Foreign Application Priority Data
Nov. 17, 2008 (GB) .................................. 0821010.6

(51) Int. Cl.
*A01N 37/28* (2006.01)
(52) U.S. Cl.
CPC ...................................... *A01N 37/28* (2013.01)
(58) Field of Classification Search
CPC ..................................................... A01N 37/28
USPC .......................................................... 504/130
See application file for complete search history.

(56) References Cited

U.S. PATENT DOCUMENTS

| 4,792,560 A | 12/1988 | Huang |
| 5,952,369 A * | 9/1999 | Ito .................................. 514/424 |
| 2008/0274082 A1 | 11/2008 | Gai et al. |
| 2009/0123423 A1 | 5/2009 | Gai et al. |

FOREIGN PATENT DOCUMENTS

| EP | 0405808 | 1/1991 |
| WO | 96/30339 | 10/1996 |
| WO | 03048138 | 6/2003 |
| WO | 2007141009 | 12/2007 |

OTHER PUBLICATIONS

Huang, F.C, Differential Effects of a Series of Hydroxamic Acid Derivatives ofn 5-Lipoxygenase and Cyclooxygenase..Effects on Inflammation and Anaphylaxid, 1989, Journal of Med. Chem, vol. 32, pp. 1836-1842.*
Martin J. Sergent, et al: "Selective Inhibition of Carotenoid Cleavage Dioxygenases." Journal of Biological Chemistry, vol. 284, No. 8, Dec. 19, 2008, pp. 5257-5264.
Beilstein Institute for Organic Chemistry, Frankfurt-Main, DE; 2001, Database accession No. 8938159, 8937019, 8937676, 8937672 abstract & Bioorganic & Medicinal Chemistry.
Beilstein Institute for Organic Chemistry, Frankfurt-Main, DE; 1992, database accession No. 5428245 abstract & J. Am. Chem. Soc., vol. 114, No. 15, 1992.
Beilstein Institute for Organic Chemistry, Frankfurt-Main, DE; 2003, database accession No. 9553211 abstract & J. Org. Chem., vol. 68, No. 12, 2003, pp. 4876-4885.
Beilstein Institute for Organic Chemistry, Frankfurt-Main, DE; 1990, Database accession No. 3546951, 3549412 abstract & J. Med. Chem., vol. 33, No. 3, 1990, pp. 993-998.
Beilstein Institute for Organic Chemistry, Frankfurt-Main, DE; 1989, Database accession No. 6516010, 6524161, 6509305 abstract & J. Med. Chem., vol. 32, No. 8, 1989, pp. 1836-1842.

* cited by examiner

*Primary Examiner* — Sue Liu
*Assistant Examiner* — Andriae M Holt
(74) *Attorney, Agent, or Firm* — R. Kody Jones

(57) ABSTRACT

A method of stimulating germination in plant seeds and/or releasing plant tissue or plant organs from dormancy, comprising applying to a seed, plant, plant organ or plant tissue a compound of formula (I): where: $R_1$ is alkyl or H; $R_2$, $R_3$, $R_4$ and $R_5$ are independently selectable from H, halide, $-NO_2$, $-SO_2R'$, $-OH$, $-Oalkyl$ where R' is alkyl or aminoalkyl; and/or $R_1$ and $R_5$ are joined as $-O(CH_2)_m-$, where m is 1, 2, 3 or 4; $R_6$ is a substituted or non-substituted alkyl, and/or substituted or non-substituted aryl; and n is an integer of 1 to 4.

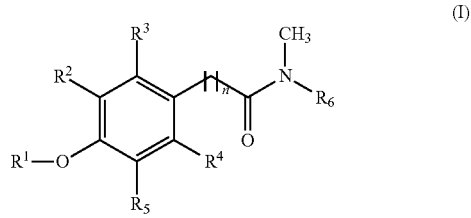

(I)

21 Claims, 6 Drawing Sheets

PLANT DEVELOPMENT CONTROL COMPOSITION

This application is a 371 of International Application No. PCT/GB09/002686 filed Nov. 17, 2009, which claims priority to GB 0821010.6 filed Nov. 17, 2008, the contents of which are incorporated herein by reference.

The invention relates to new compounds, new compositions and their uses for the stimulation of germination and release from dormancy of plant seeds, tissues and plants.

Carotenoids are synthesised in plants and micro-organisms as photoprotective molecules and are key components in animal diets, an example being β-carotene (pro-vitamin A). The oxidative cleavage of carotenoids occurs in plants, animals, and micro-organisms and leads to the release of a range of apocarotenoids that function as signalling molecules with a diverse range of functions (1). The first gene identified as encoding a carotenoid cleavage dioxygenase (CCD)[1] was the maize Vp14 gene that is required for the formation of abscisic acid (ABA), an important hormone that mediates responses to drought stress and aspects of plant development such as seed and bud dormancy (2). The VP14 enzyme cleaves at the 11,12 position (FIG. 1) of the epoxycarotenoids 9'-cis-neoxanthin and/or 9-cis-violaxanthin and is now classified as a 9-cis-epoxycarotenoid dioxygenase (NCED) (3), a subclass of the larger CCD family.

Figure 1:
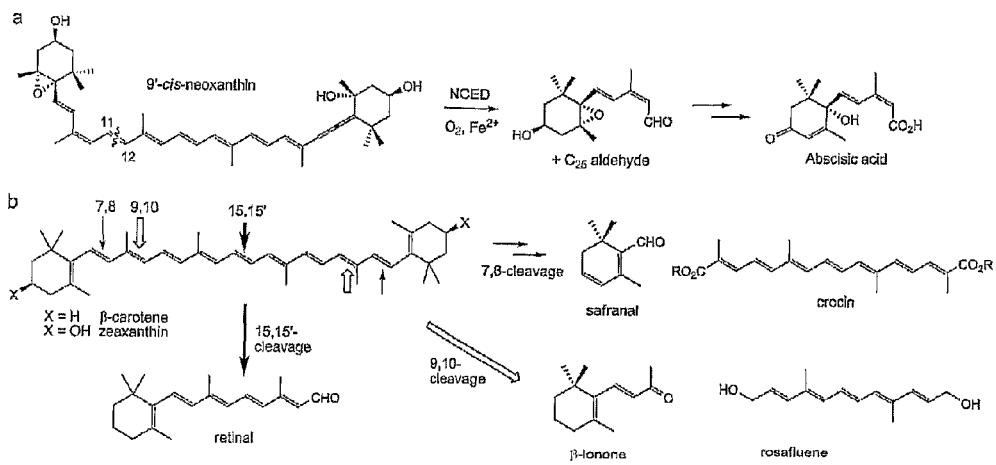

Since the discovery of Vp14, many other CCDs have been shown to be involved in the production of a variety of apocarotenoids (FIG. 1). In insects, the visual pigment retinal is formed by oxidative cleavage of β-carotene by β-carotene-15,15'-dioxygenase (4). Retinal is produced by an orthologous enzyme in vertebrates, where it is also converted to retinoic acid, a regulator of differentiation during embryogenesis (5). A distinct mammalian CCD is believed to cleave carotenoids asymmetrically at the 9,10 position (6) and, although its function is unclear, recent evidence suggests a role in the metabolism of dietary lycopene (7). The plant volatiles β-ionone and geranylacetone are produced from an enzyme that cleaves at the 9,10 position (8) and the pigment α-crocin found in the spice saffron results from an 7,8-cleavage enzyme (9).

Other CCDs have been identified where biological function is unknown, for example in Cyanobacteria where a variety of cleavage specificities have been described (10-12). In other cases there are apocarotenoids with known functions, but the identity or involvement of CCDs have not yet been described: grasshopper ketone is a defensive secretion of the flightless grasshopper *Romalea microptera* (13), mycorradicin is produced by plant roots during symbiosis with arbuscular mycorrhyza (14), and strigolactones (15) are plant metabolites that act as germination signals to parasitic weeds such as *Striga* and *Orobanche* (16).

Recently it was discovered that strigolactones also function as a branching hormone in plants (17,18). The existence of such a branching hormone has been known for some time, but its identity proved elusive. However, it was known that the hormone was derived from the action of at least two CCDs, max3 and max4 (more axillary growth) (19), because deletion of either of these genes in *Arabidopsis thaliana*, leads to a bushy phenotype (20,21). In *E. coli* assays, AtCCD7 (max3) cleaves β-carotene at the 9,10 position and the apocarotenoid product (10-apo-β-carotene) is reported to be further cleaved at 13,14 by AtCCD8 (max4) to produce 13-apo-β-carotene (22). Also recent evidence suggests that AtCCD8 is highly specific, cleaving only 10-apo-β-carotene (23). How the production of 13-apo-β-carotene leads to the synthesis of the complex strigolactone is unknown. The possibility remains that the enzymes may have different specificities and cleavage activities in planta. In addition, a cytochrome P450 enzyme (24) is believed to be involved in strigolactone synthesis and acts in the pathway downstream of the CCD genes. Strigolactone is thought to effect branching by regulating auxin transport (25). Because of the involvement of CCDs in strigolactone synthesis, the possibility arises that plant architecture and interaction with parasitic weeds and mycorrhyza could be controlled by the manipulation of CCD activity.

Although considerable success has been obtained using genetic approaches to probe function and substrate specificity of CCDs in their native biological contexts, particularly in plant species with simple genetic systems or that are amenable to transgenesis, there are many systems where genetic approaches are difficult or impossible. Also, when recombinant CCDs are studied either in vitro or in heterologous in vivo assays, such as in *E. coli* strains engineered to accumulate carotenoids (26), they are often active against a broad range of substrates (5,21,27), and in many cases the true in vivo substrate of a particular CCD remains unknown. Therefore additional experimental tools are needed to investigate both apocarotenoid and CCD functions in their native cellular environments.

In the reverse chemical genetics approach, small molecules are identified that are active against known target proteins; they are then applied to a biological system to investigate protein function in vivo (28,29). This approach is complementary to conventional genetics since the small molecules can be applied easily to a broad range of species, their application can be controlled in dose, time and space to provide detailed studies of biological functions, and individual proteins or whole protein classes may be targeted by varying the specificity of the small molecules. Notably, functions of the plant hormones gibberellin, brassinosteroid and abscisic acid have been successfully probed using this approach by adapting triazoles to inhibit specific cytochrome P450 monooxygenases involved in the metabolism of these hormones (30).

In the case of the CCD family, the tertiary amines abamine (31) and the more active abamineSG (32) were reported as specific inhibitors of NCED, and abamine was used to show new functions of abscisic acid in legume nodulation (33).

The inventors have identified a group of compounds which stimulate germination and release plant tissues or plant organs from dormancy.

The Invention therefore provides a method of stimulating germination in plant seeds and/or releasing plant tissue from dormancy, comprising applying to a seed, plant tissue, plant organ or a plant a compound of formula I.

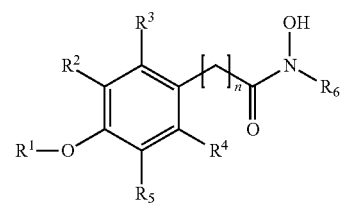

where:
$R_1$ is alkyl or H;
$R_2$, $R_3$, $R_4$ and $R_5$ are independently selectable from H, halide, —$NO_2$, —$SO_2R'$, —OH, —Oalkyl where R' is alkyl or aminoalkyl; and/or $R_1$ and $R_5$ are joined together as —$O(CH_2)_m$— (so that the full group attached to the aryl group is —$O(CH_2)_mO$—, where m is 1, 2, 3 or 4, especially 1, where;

$R_6$ is hydrophobic group, such as a substituted or non-substituted alkyl, and/or substituted or non-substituted aryl; and n is an integer of 1, 2, 3 or 4 n may be 1. The group linking the aryl group to the carbonyl group of the hydroxamic acid part of the molecule, —$(CH_2)_n$—, may also be substituted with, for example, —OH, halide or methyl.

$R_1$ is preferably a $C_1$-$C_4$ alkyl, such as methyl, ethyl, propyl or butyl. $R_1$ may also be H. $R_2$, $R_3$, $R_4$ and $R_5$ may all be H. Alternatively, one, two or three of those side groups may be H, the other side groups being alternative side groups. The alkyl moiety of the —Oalkyl group is preferably a $C_1$-$C_4$ alkyl, such as methyl, ethyl, propyl or butyl.

$R_5$ may be Omethyl. The remaining substituents, $R_2$, $R_3$ and $R_4$ may be H where $R_5$ is —Omethyl.

$R_6$ is preferably a hydrophobic group. $R_6$ may be a $C_1$-$C_{12}$ alkyl, most preferably a $C_5$-$C_{10}$ alkyl. $R_6$ may be any one of a $C_1$, $C_2$, $C_3$, $C_4$, $C_5$, $C_6$, $C_7$, $C_8$, $C_9$, $C_{10}$, $C_{11}$ or $C_{12}$ alkyl. $R_6$ may also be an aryl group or —$(CH_2)_p$ aryl, where p=an integer of 1 to 4 and aryl is substituted or non-substituted. n is preferably 1.

$R_6$ may be a substituted alkyl or a substituted aryl. The alkyl or aryl groups may be substituted with one or more halides, —OH, —$NO_2$ or —$SO_2R'$.

Preferably the compound comprises $R_6$ of formula II.

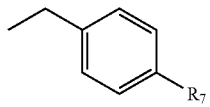

wherein $R_7$ is —H, —OH, —$NO_2$, —$SO_2R'$ or halide.

As used herein, the term "halide" includes fluorine, chlorine, bromine or iodine, most preferably fluorine.

The length of the hydroxamic acid linker to the hydrophobic group has been shown to be important and affects the activity of the compounds.

The methods may comprise adding the compound to one or more seeds prior to sowing. The seed, may alternatively be treated in situ after sowing in a medium such as soil, compost or other growing medium.

The composition may be used to treat weed seeds, to encourage them to germinate. This means that they are then killed with a treatment of herbicide to allow the ground to be more readily cleared of weeds prior to planting crops. Weeds may also be killed by tillage.

Other plant material, such as tubers, corns or bulbs may also be treated to stimulate growth before or after planting.

The method may comprise treating plant tissues, organs or plants to stimulate fruiting or flowering.

Using the compounds has a number of advantages:
(i) Growth can occur earlier in plants as plant tissues or organs are released from dormancy earlier than normal, without affecting carotenoid sysnthesis, a problem with some known compounds.
(ii) Buds, such as ornamental flowers and fruit flowers can be stimulated to allow bud growth to be stimulated or uniformally controlled.
(iii) Seeds, tubers, corns, bulbs and other propagating material may be stimulated into germination and growth. This may be used to treat primary dormancy in seeds and reduce secondary dormancy due to non-favourable conditions such as high temperature or sub-optimal soil moisture content.
(iv) Uniformity of germination increases crop value and uniformity. An increased canopy development with the improved crop development increases water use efficiency by preventing water loss from bare soil and then suppresses weed growth.
(v) The use of the compounds may have an effect on plant breeding:

Strong dormancy is a negative trait where rapid and uniform crop establishment and development are required. However, prolonged dormancy is a positive attribute for storage of the harvestable parts of crops because sprouting of stored produce will lead to mobilization of reserves and metabolic changes that reduce quality and value of the produce.

Breeding programs often lead to reduction in natural dormancy (to allow rapid cycling between generations), and then chemical means are used to prevent dormancy break in stored produce. For example, long-term storage of potato tubers and onion bulbs requires cold-storage, and/or application of mitotic growth inhibitors to prevent sprouting. In cereals, in some environmental conditions, seeds will germinate on the ear before harvest (pre-harvest sprouting), leading to poor quality crops.

These compounds could be used to reverse this situation; high levels of dormancy could be bred into crops varieties to allow good storage without chemical interventions, but the compounds would then need to be applied to dormant tissues (seeds, corms, bulbs, buds) to promote crop establishment and growth. This has been demonstrated in the case of SP12 tomato seed (modified for high ABA content, see below); seeds have prolonged dormancy and this is reversed by application of the compounds. Chemical treatment at the crop establishment phase rather than of the stored, harvested crop would reduce exposure of consumers to agrochemicals.

Plants have been genetically modified (and could also be bred conventionally), to have higher ABA content and this resulted in increased water use efficiency and/or drought resistance [Thompson, A. J., et al., *Over-production of abscisic acid increases water-use efficiency and root hydraulic conductance and influences leaf expansion*. Plant Physiology, 2007. 143: p. 1905-1917.7]. However, such plants may also have higher dormancy. Application of these compounds would allow dormancy in such plants to be overcome, making them of greater utility.

In breeding of crops that have difficult to overcome dormant phases, these compounds may accelerate the breeding process by their ability to break dormancy and so shortening the generation time (e.g. seed to seed time) in the breeding program.

The invention also provides plant compositions comprising compounds of formula I and also to isolated compounds of formula I, where the compound is as defined above.

The compositions and formulation used in the invention additionally comprise one or more adjuvants. Adjuvants for use in herbicidal compositions are generally known in the art. These include oil-based adjuvants and mixtures, organosilicone-based adjuvants and mixtures, non-ionic based adjuvants and mixtures, polymeric-based adjuvants and mixtures, and fatty acid-based adjuvants and mixtures, and combinations thereof. Mineral oil may be added as an adjuvant. The adjuvants may be added as 1%-95% by weight of the active ingredients.

The herbicidal composition may also comprise, or additionally comprise, a solid material, such as a clay, silica or other inert solid carrier generally known in the art.

The herbicidal composition may be applied as a solid or a liquid. The liquid media used may be, for example, kerosene, xylene, an alcohol such as ethanol. Mixtures of such liquids may be used. These may be utilised in combination with surface active agents such as detergents, to improve the wetting of the plant or seed.

The composition may comprise one or more seed encapsulation agents or film forming agents. Such agents are generally known in the art and may be admixed with the compound of formula I or applied subsequent to treatment of the seed.

Seeds may be treated with the compound by drum priming or seed coating methods generally known in the art and dried.

Seed encapsulation and film forming agents include gypsum, diatomaceous earth and bertonite clay together with binders. Polymers and gels, such as alginates and copolymers of polyvinyl pyrrolidone/vinyl acetate or nucleic acid/alkyl vinyl ether are generally known.

Pelleting of the seed with a matrix of a filling material and a glue may also be carried out. Known pelleting materials include loam, starch and polyacrylate/polyacrylamide polymers. Fungicides, pesticides and/or bulking materials may also be added.

Seeds, plant tissues, plant organs and plants treated with the composition of the invention, are also provided by the invention.

The plant may be a monocotyledonous or dicotyledonous plant. It is preferably selected from tomato, potato, onion, wheat, barley, oats, sorgum, maize, rice, Brassica sp., vegetable and salad crop seeds including parsnip, lettuce, spinach, chicory and leek, and any species of trees and shrubs.

The herbicidal formulation may be applied directly onto the plant or applied to the soil.

The compositions are known to be effective at, for example, 1 mM concentration. Preferably concentrations above 2 mM are not used as this may have reduced effectiveness.

A further aspect of the invention provides an isolated compound of formula I, as defined above.

The invention will now be described by way of example only, with reference to the following figures.

FIGURE LEGENDS

FIG. 1.

Reactions catalysed by the carotenoid cleavage dioxygenases: a, 11,12-oxidative cleavage of 9'-cis-neoxanthin by NCED; b, oxidative cleavage reactions on β-carotene and zeaxanthin.

FIG. 2.

Synthetic route for preparation of hydroxamic acids and inhibitors.

FIG. 3.

Inhibitor design. Protonated abamine (a), a carotenoid carbocation intermediate (b) and a hydroxamic acid inhibitor (c) are shown bound to iron(II) cofactor of a CCD.

FIG. 4.

The relative inhibition of four CCDs in E. coli. CCD genes were expressed in E. coli. strains that produce β-carotene. The strains were grown in the presence or absence of inhibitors (100 μM) for 16 hours. This concentration of inhibitor was within the linear range of the E. coli. response. The relative inhibition of each class of CCD was determined by the increase in β-carotene accumulation in the presence of the inhibitor, a value of 0 would indicate β-carotene levels equal to when no inhibitor was present and a value of 100 would equal the maximum level of β-carotene as observed in strains lacking a CCD (see Experimental Procedures for equation). Error bars represent the standard error of the mean, n=4. The floating black bar represents the least significant difference (P<0.05) for comparison of any two means.

FIG. 5.

The effect of inhibitors on the outgrowth of buds from excised *Arabidopsis* nodes in the presence of 1 μM NAA. The graph shows lag time before the commencement of bud outgrowth for Col-0 (WT) in the presence or absence of 100 μM inhibitor. A null mutant of AtCCD7I (max3) was included without inhibitor as control. Values represent means from five independent experiments; n=35 (WT), n=18 (max3), n=14-16 (WT plus inhibitors). The floating black bar represents the least significant difference for comparison of any two means, and asterisks indicate values significantly different from the WT (P<0.05).

FIG. 6.

Branching phenotypes of *Arabidopsis* plants grown in agar media for 45 days supplemented with inhibitor D6. Images are shown: (a) Col-0 (WT) without inhibitor; (b) max3-9 mutant without inhibitor; (c) Col-0 with 100 μM D6. The numbers (d) of rosette branches were quantified. Error bars represent standard error of the mean, n=6 to 12.

FIG. 7.

The amount of β-carotene present (expressed as $\mu g\ ml^{-1}$ of culture) in β-carotene accumulating *E. coli* strains expressing CCDs in the presence of inhibitor. The strains were grown in the presence or absence of inhibitors (100 μM) for 16 hours (see method section in the main manuscript). Error bars represent the standard error of the mean, n=4. (A) AtCCD7 (B) LeCCD1 (C) MmBCO2 (D) MmBCO1

FIG. 8

Effect of 100 μM D4 on germination of tomato seed that over-express NCED (line SP12). In some treatments norflurazon was added at 3.3 μM. The upper and lower panels show two independent experiments. Each germination assay included 20 seeds in one Petri dish. Error bars represent the range between duplicate dishes. The D4 treatments also contained 1% DMSO, the solvent for the D4 stock solution. The control treatment was 1% DMSO alone.

FIG. 9

Germination of either wild-type (WT; Ailsa Craig $Tm2^a$) or SP12 seed at different concentrations of D4. Each germination assay included 20 seeds in one Petri dish. Error bars represent the range between duplicate dishes. All D4 treatments also contained 1% DMSO. The control treatment was 1% DMSO without D4.

EXPERIMENTAL PROCEDURES

Synthesis of tertiary amine inhibitors—Abamine was synthesised according to published procedures (31,34).

Figure 2:
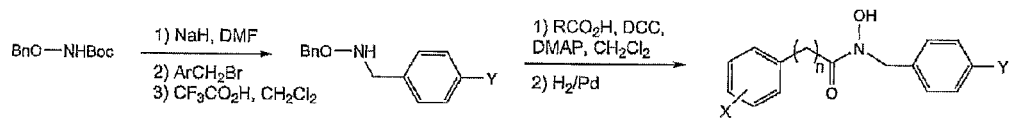

Synthesis of hydroxamic acid inhibitors—Synthesis is shown in FIG. 2 and structures are given in Table 1. N-Boc, O-benzyl-hydroxylamine was treated with NaH in DMF, followed by the appropriate benzyl or alkyl bromide (35). Deprotection was carried out by treatment with 1% trifluoroacetic acid in dichloromethane, to give the N-substituted hydroxylamine. Hydroxamic acid formation was carried out using DCC (1.1 equiv.) and 4-dimethylaminopyridine (0.2 equiv.) and the appropriate carboxylic acid, in dichloromethane. The hydroxamic acid products were purified by silica gel column chromatography. B1, D12 and D13 were prepared by activation of the appropriate acid with methyl chloroformate and triethylamine in THF, and reaction with hydroxylamine hydrochloride. The intermediate for synthesis of B1 was synthesised from β-ionone (36); B1 was isolated as a 2:1 mixture of E/Z isomers. Spectroscopic data and yields for analogues D1-D13, F1-4, and B1 are available as supplemental data.

In vitro NCED enzyme assay—We over-expressed LeNCED1 in *E. coli*, as an N-terminal His$_6$-fusion protein (supplemental methods). Cell-free extract containing recombinant LeNCED1 was prepared in 100 mM bis-tris buffer (pH 6.7). 15 µl extract was pre-activated by addition of iron(II) sulphate (20 mM, 1 µl) and ascorbic acid (20 mM, 1 µl) on ice for 2 min, prior to use. This aliquot of enzyme was then added to an assay (150 µl total volume) containing 100 mM bis-tris buffer (pH 6.7), 0.05% v/v Triton X-100, 1.0 mg/ml catalase, and 3 µg 9'-cis-neoxanthin. The 9'-cis-neoxanthin substrate was prepared as described in supplemental methods. The enzyme assay was incubated for 15 min in the dark at 20° C. Water (700 µl) was then added, and the products extracted with ethyl acetate (3×1 ml). The organic solvent was removed at reduced pressure, the residue was dissolved in methanol (200 µl), and then 100 µl was injected onto a Phenomenex $C_{18}$ reverse phase HPLC column, and a gradient of 5-10% methanol in acetonitrile/0.05% triethylamine was applied at 0.5 ml/min over 20 min, detecting at 440 nm. NCED inhibition assays contained 1-100 µM inhibitor; inhibition was calculated from the product formation after 15 min, compared to a control assay with no inhibitor present. Retention times: 9'-cis-neoxanthin, 10.2 min; $C_{25}$ product, 6.5 min.

In vitro LeCCD1a enzyme assay—We over-expressed LeCCD1a in *E. coli*, as a GST-fusion protein (supplemental methods). The in vitro assay of LeCCD1a was based on reported methods (37), and was carried out in a 200 µl total volume in a 96-well microtitre plate, with the signal detected at 485 nm. To prepare substrate solution for each assay, 5 µl of 4% (w/v in ethanol) apo-8'-carotenal (Sigma) was mixed with 25 µl of 4% (w/v in ethanol) β-octylglucoside (Sigma), the ethanol was then evaporated under nitrogen, and the residue dissolved in 150 µl PBS buffer containing 10 mM sodium ascorbate by incubation at 20° C. for 30 min. 50 µl of cell-free extract containing recombinant LeCCD1a was added, and the reactions monitored over 30 min at 20° C.

In vivo enzyme assays in *E. coli*—The genes of interest (supplemental Table S1) were cloned into the vector pET30c (Novagen) fused directly to the initial ATG codon with no tag, or into pGEX-4T such that the gene was fused to an N-terminal GST tag. All genes were full length except AtCCD7, which had the chloroplast signal sequence removed (supplemental methods). This gene, when fused to GST in the pGEX-4t vector (GE Healthcare), showed greater CCD activity than when expressed in a pET vector without a tag. Therefore, this construct was used in subsequent assays. The plasmids were transferred to the *E. coli* expression strain BL21(DE3), harbouring pAC-BETA (38), and therefore producing β-carotene.

Figure 8:
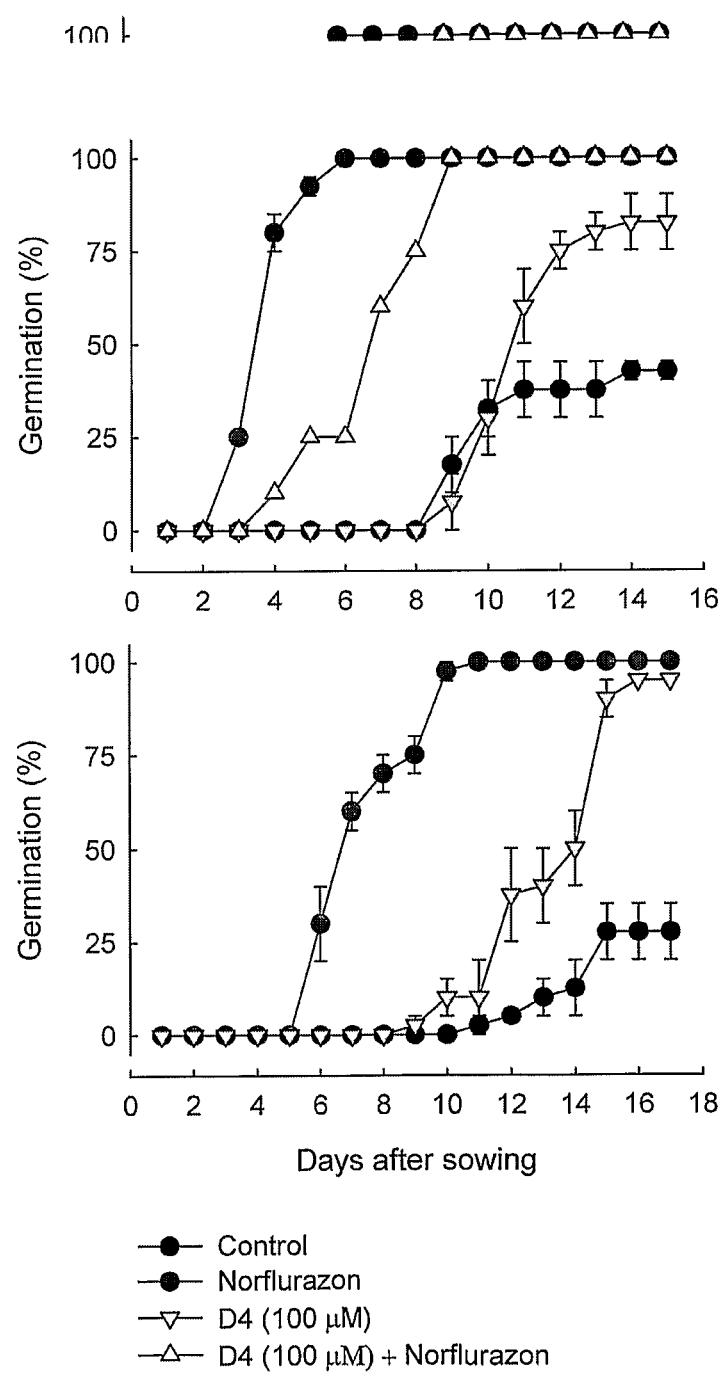

For each inhibitor assay, 2.5 ml LB media with the appropriate antibiotics (25 µg ml$^{-1}$ chloramphenicol and 50 µg ml$^{-1}$ kanamycin or 100 µg ml$^{-1}$ ampicillin) and 2.5 µM IPTG, was prepared. Inhibitors (0.1 M in 100% ethanol) were added to the media to a final concentration of 100 µM. The media was then inoculated with 0.25 ml of overnight culture (grown at 37° C. with the appropriate antibiotics) and incubated with shaking (200 rpm) at 28° C. for 16 hours. One ml of culture was harvested by microcentrifugation and resuspended thoroughly in 1 ml ethanol containing 0.2% Triton X-100. After vortexing, the extract was incubated at room temperature in the dark for 3 hours, again vortexed and then spun in a microcentrifuge for 5 min at 13000 rpm. The supernatant was removed and the O.D.$_{453}$-O.D.$_{550}$ was measured. The amount of β-carotene was calculated using a standard curve generated from a dilution series of β-carotene (Sigma) in ethanol with 0.2% Triton X-100; the absolute levels of β-carotene are shown in FIG. 8. The relative inhibition was calculated by the equation: $(C_i - C_c)/(C_1 - C_c) \times 100$, where $C_i$ is the carotenoid level with inhibitor and CCD present, $C_c$ is the level with CCD but without the inhibitor and $C_1$ is the level in a strain where lacZ is expressed instead of the CCD, and no inhibitor is present. Thus the increase in β-carotene due to inhibition of the CCD ($C_1 - C_c$) was expressed relative to the maximum possible β-carotene content when CCD is absent ($C_1 - C_c$).

Axillary bud outgrowth assay in *Arabidopsis* stein sections—The assays were performed essentially as described (40) with the following modifications. Small Petri dishes (50 mm diameter, 20 mm depth) were filled with 10 ml of ATS (39) supplemented with 1% agar and 1% sucrose. Inhibitors and α-naphthalene acetic acid (NAA) were added to the agar before pouring to give 100 µM and 1 µM, respectively. Thus, when the central strip was cut out of the agar, both the apical and basal media contained both NAA and inhibitor. Any nodes in which the apical end had curled out of the media or which bud length was less than 2 mm at the end of the experiment were discounted. Measurement of the shoot length was performed every 24 hours. For each assay a logistic curve was fitted using Genstat ($10^{th}$ edition, VSN international) with the fitcurve directive and the lag phase was calculated by extrapolating the linear part of the curve and the initial plateau (see supplementary methods). The x value of where these two lines intersected represented the lag phase.

Figure 4:
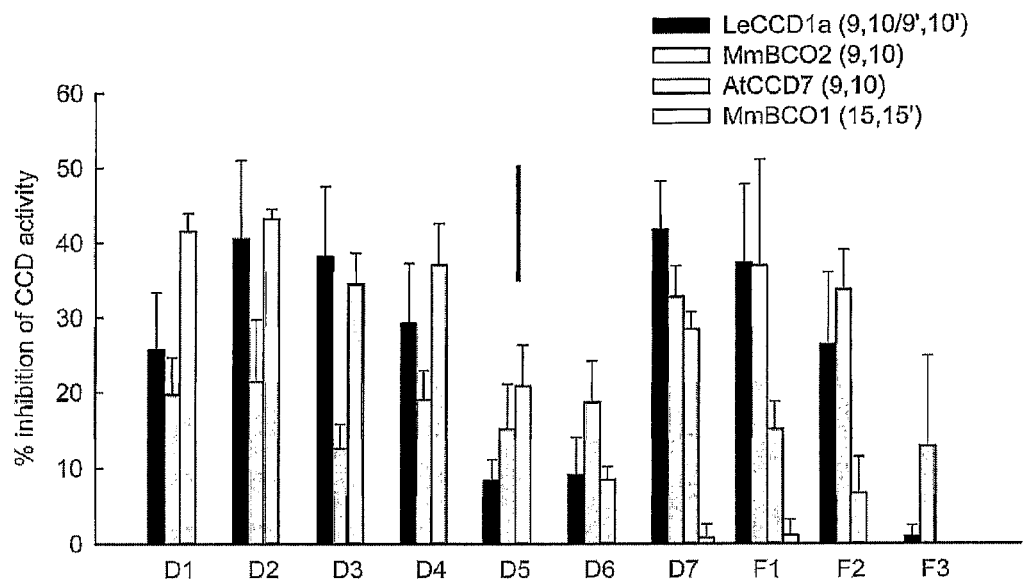
Figure 5:
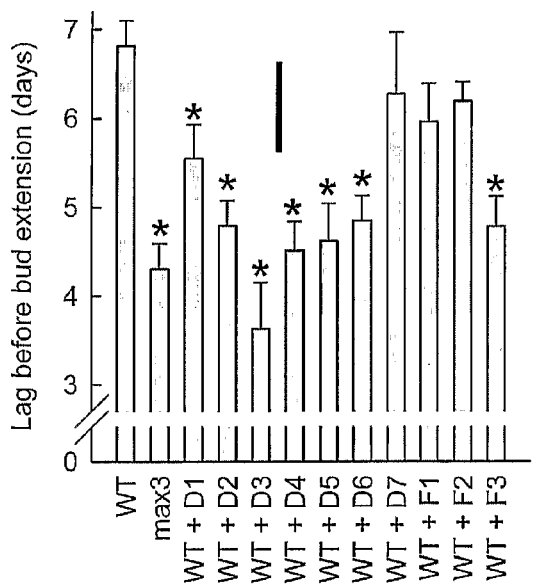

Statistical analysis—For data in FIGS. 4 and 5 analysis was by Residual Maximum Likelihood (REML) in Genstat10. In both cases an F-test showed that overall the treatment effects were highly significant (P<0.001). The maximum value of the least significant difference (LSD) was calculated by multiplying the maximum standard error of differences by a t-value (P=0.05), and is presented on the graphs. There were 105 and 157 degrees of freedom for the LSDs shown in FIGS. 4 and 5 respectively. The maximum LSD was used because individual LSDs varied but if differences between means were significant using the maximum values then they were also significantly different at the individual value for any two selected means.

Seed Material

Seeds used were "wild-type" tomato (*Solanum lycopersicum* cv. Ailsa craig near-isogenic line containing the Tm2$^a$ tobacco mosaic virus resistance gene). In addition, we used transgenic tomato seed (*Solanum lycopersicum* cv. Ailsa craig) transformed with a construct designed to over-express the gene LeNCED1, encoding 9-cis-epoxycarotenoid dioxygenase. These transgenic seeds are known as D9 [Thompson, A. J., et al., *Ectopic expression of a tomato 9-cis-epoxycarotenoid dioxygenase gene causes over-production of abscisic acid*. Plant Journal, 2000. 23(3): p. 363-745], but were later renamed as SP12 [Thompson, A. J., et al., *Regulation and manipulation of ABA biosynthesis in roots*. Plant Cell and Environment, 2007. 30: p. 67-78.6], and they have previously been shown to have delayed and low percentage final germination due to the over-production of abscisic acid caused by the over-expression of LeNCED1 [Thompson, A. J., et al., *Ectopic expression of a tomato 9-cis-epoxycarotenoid dioxygenase gene causes over-production of abscisic acid*. Plant Journal, 2000. 23(3): p. 363-74.5].

Germination Assays

Each assay consisted of a 10 cm vented Petri dish containing an 8.5 cm diameter circle of Whatman Grade 1 filter paper (Whatman International Ltd, Maidstone, England) soaked in 1 ml of test solution. Seeds were surface sterilized with 30% household bleach for 30 mins, rinsed in distilled water, and then 20 seeds were placed on the filter paper in each Petri dish. The Petri dishes were incubated at high relative humidity (>95%) at 25° C. in the dark. Seed germination, defined as visible emergence of the radicle, was scored daily. Replicate plates were used for each chemical treatment.

Hydroxamic acids were dissolved in dimethylsulphoxide (DMSO), and aqueous test solutions were prepared such that the final concentration of DMSO was 1% v/v. Control solution consisted of 1% v/v DMSO in water. Norflurazon was prepared as a stock solution at 20 mg ml$^{-1}$ in ethanol, and then diluted with water to a final concentration of 5 mg l$^{-1}$, with ethanol present at 0.025% v/v.

Supplemental Methods
Strain Construction

Plasmids were prepared using Qiaprep plasmid mini spin kits (Qiagen) and PCR products and cut vector were purified using QiaQuick columns (Qiagen), following manufacturer's instructions. PCR was carried out using HiFi Expand (Roche) DNA polymerase following manufacturer's instructions. Ligations were performed with T4 DNA ligase (Invitrogen) for 1 hour at 25° C. Constructs were initially cloned into *E. coli* DH10B cells (Stratagene) and were sequenced to ensure that no PCR errors had taken place.

The LeCCD1a gene (AY576001) was amplified from cLET29I6 (obtained from The Institute for Genomic Research (TIGR) tomato gene index) using primers LeCCD1a-FC1:-TACGAATTCCATATGGGGAGAAAA-GAAGATG and LeCCD1a-RC1:-TAGTCTCGAGTCA-CAGTTTGGCTTGTTC. The product was cut with NdeI and XhoI and ligated into similarly cut pET30c (Novagen, VWR International, Ltd). In addition, the product was cut with EcoR1 and Xho1 and ligated into the similarly cut pGEX-4T (GE Healthcare).

The AtCCD7 gene was amplified from pCR2.1-AtCCD7, kindly supplied by Ottoline Leyser (University of York), using the primers AtCCD7-FC3 TATGCTCGAG-GAGATCTGGATTAATGGCCGCAATATCAATATC and AtCCD7-RC 1 TAGTCTCGAGTCAGTCGCTAGCCCAT-AAAC. The PCR product was cut with BglII and Xho1 and cloned into BamHI/SalI-cut pGEX-4T.

The MmBCO1 (AF294899) was amplified from the clone IMGCLO2192191 obtained from Geneservice Ltd. (Cambridge, UK) using the primers MmBCO1-FC1 TACTGAAT-TCCATATGGAGATAATATTTGGC and MmBCO1-RC1 TACTCTCGAGTGAGTGTTAGGATTAAAG. The PCR product was cut with NdeI/XhoI and cloned into similarly cut pET30c.

The MinBCO2 gene (AJ290392) was amplified from the clone IMGCLO2536812 (Geneservice Ltd.) using the primers MmBCO2-FC1 TATCGGATCCCATATGTTGGGAC-CGAAGCAGAG and MmBCO2-RC1 TATCCTCGAG TCAGATAGGCACAAAGGT. The product was cut with NdeI/XhoI and cloned into similarly cut pET30c.

The LeNCED1 cDNA (Z97215) was provided by Ian Taylor (University of Nottingham) and was cloned into the NdeI and Bpu1102 sites of vector pET14b (Novagen, VWR International, Ltd) to provide an N-terminal fusion to a His$_6$ tag. The plasmid was expressed in *E. coli* Rosetta (DE3) cells (Novagen, VWR International, Ltd).

Details of strains used for inhibitor assays in *E. coli* are also given in Supplemental Table S1, below.

Preparation of Cell-Free Extracts

For the production of cell-free extracts of LeCCD1a and LeNCED1, cultures were grown to an OD of 0.6 at 37° C., then isopropyl β-D-1-thiogalactopyranoside (IPTG) was added to 0.2 mM and the cultures grown overnight at 20° C. The cells (200 ml cultures) were harvested by centrifugation (5000 rpm, 10 min) and the pellet re-suspended in 4 ml PBS, 0.1% Triton-X 100. Lysozyme was added to a final concentration of 25 μg ml$^{-1}$ and the solution incubated at room temperature for 15 min before sonication (3×30 s at 18Ω) on ice. The lysate was then centrifuged (13000 rpm, 15 min, 4° C.) and the supernatant used for the assay.

Calculation of Lag Phase for Shoot Elongation Assays

A logistic curve, $y=A+C/(1+e^{-B(t-m)})$, was fitted to the data for each shoot using GenStat (10$^{th}$ edition). The lag phase was then calculated using the equation m−(2/B) which effectively gave the t value (time) of the intercept of the two extrapolated lines from the linear part of the curve and the initial plateau.

Preparation of 9'-cis-neoxanthin

Fresh spinach (20 g) was washed and crushed with BHT (0.03 g) and sodium bicarbonate (0.3 g) in cold methanol (30 ml) using a pestle and mortar for 3 min in the dark, and the mixture was then filtered under suction. This was repeated 6 times until the retentate became nearly colourless. The combined extract was partitioned between cold diethyl ether and saturated sodium chloride. The ether extract was collected, and the aqueous layer was re-extracted twice with cold diethyl ether. The ether extracts were combined, and solvent was removed by rotary evaporation below 32° C. The residue was saponified with 6% KOH in 9 ml of methanol and 1 ml of diethyl ether in the dark at 4° C. for 16 hr. Saturated aqueous sodium chloride solution (50 ml) was added, extracted with diethyl ether (100 ml×3), dried over Na$_2$SO$_4$, and solvent was removed as above. 9'-cis-neoxanthin was then purified by column chromatography, using deactivated alumina (10 g alumina, mixed for 5 minutes with 1 ml distilled water and 10 ml petroleum ether). The solid spinach extract was applied in diethyl ether/petroleum ether (1:5), and the column washed with diethyl ether/petroleum ether (1:1, 50 ml), diethyl ether (50 ml), and 5% ethanol in diethyl ether (50 ml), which finally eluted 9'-cis-neoxanthin. The 9'-cis-neoxanthin fraction was dried with nitrogen and stored in vials wrapped with foil under nitrogen at −20° C. Data: R$_f$ 0.09 (silica, Et$_2$O); I$_{max}$ 415, 439, 467 nm; m/z (FAB$^+$) 600.33, calc. 600.87 for C$_{40}$H$_{56}$O$_4$.

Results

Inhibitor design and synthesis—NCED was proposed to be a dioxygenase (3), with a reaction mechanism involving a carbocation intermediate, followed by formation of a dioxetane ring or a Criegee rearrangement prior to cleavage (41); such a mechanism was supported by $^{18}$O labelling experiments with AtCCD1 (37), and was the most likely mechanism based on computational studies of the ACO crystal structure (42).

Figure 3:
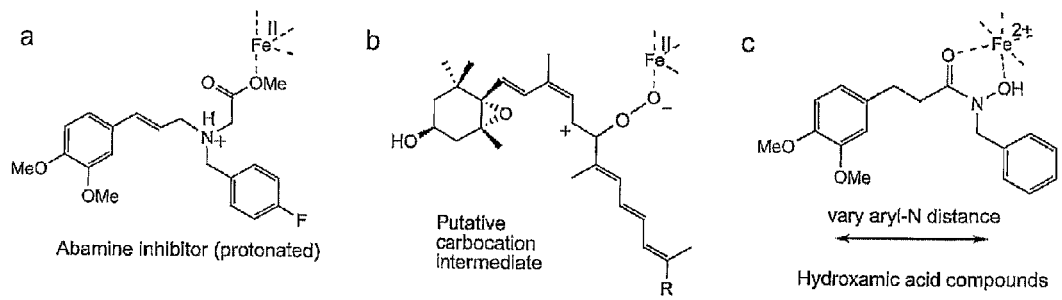

It was reported that the tertiary amine abamine (see FIG. 3a for structure) is a reversible competitive inhibitor (K$_i$=39 μM) of recombinant NCED and that it inhibited abscisic acid production in planta at 50-100 μM concentration (31). AbamineSG, with an extended 3 carbon linker between the methyl ester and the nitrogen atom, was subsequently developed with an improved activity (K$_i$=18.5 μM) (32). The precise mechanism of action of abamine is uncertain, but our hypothesis was that the protonated amine mimics a carbocation intermediate in the catalytic mechanism, with the oxygenated aromatic ring bound in place of the hydroxy-cyclohexyl terminus of the carotenoid substrates (41), as shown in FIG. 3. Inhibition may be due in part to chelation of the essential metal ion cofactor by the methyl ester of abamine However, a derivative of abamine, containing an acid group (COOH) in place of the methyl ester, was not active (32), even though in theory this should be more effective at binding the iron cofactor Hydroxamic acids are known to act as inhibitors of several different classes of metalloenzymes, such as the matrix metalloproteases, by chelation of the essential metal ion cofactor (43). Therefore, hydroxamic acid analogues were synthesised, in which the hydroxy-cyclohexyl terminus of the carotenoid substrate was mimicked as above by an oxygenated aromatic ring, and the hydroxamic acid functional group was positioned at variable distance from the aromatic ring. Thus, a collection of aryl-$C_3N$ analogues (D8-D13), aryl-$C_2N$ analogues (D1-D7), and aryl-$C_1N$ analogues (F1-F4) was also synthesised (Table 1). The 4-fluorobenzyl substituent, found to promote activity in the abamine series (31), was included in the collection of hydroxamic acids. The synthetic route, shown in FIG. 2, involves coupling of the appropriate acid with a substituted O-benzyl hydroxylamine, followed by deprotection. One hydroxamic acid containing a longer $C_5$ spacer from a cyclohexyl moiety (B1) was also synthesised from β-ionone. A set of 18 hydroxamic acids was then used for inhibitor screening; numbering of chemical compounds is given in Table 1.

TABLE 1

Inhibition of recombinant LeCCD1 and LeNCED1 enzymes using in vitro assays.
Enzyme assays, using *E. coli* cell extracts containing the recombinant CCD, were initially
carried out at 100 μM inhibitor concentration; for compounds showing ≥90% inhibition
of LeCCD1 at this concentration, $IC_{50}$ values were also determined. NT, not tested.
Chemical structures of hydroxamic acid inhibitors are shown below, with X and
Y given in the table. The structure of abamine is given in Fig. 3.

| | Inhibitor | | | LeCCD1a (9,10/9',10') | | LeNCED1 (11,12) |
|---|---|---|---|---|---|---|
| Class | Name | X | Y | Inhibition @ 100 μM (%) | $IC_{50}$ (μM) | Inhibition @ 100 μM (%) |
| Abamine | | | | 20, 49[a] | 210 | 20 |
| Aryl-$C_1N$ | F1 | 4-OMe | H | >95 | 2.0 | 0 |
| | F2 | 4-OMe | F | >95 | 2.5 | 0 |
| | F3 | 3,4-$(OMe)_2$ | H | 50 | | 2 |
| | F4 | 3,4-$(OMe)_2$ | F | 0 | | 0 |
| Aryl-$C_2N$ | D1 | 4-OH | H | >95 | 0.9 | 27 |
| | D2 | 4-OH | F | >95 | 0.8 | 29 |
| | D3 | 3,4-$(OH)_2$ | F | >95 | 0.8 | 4 |
| | D4 | 4-OMe | F | >95 | 2.5 | 33 |
| | D5 | 3,4-$(OMe)_2$ | H | >95 | 8.0 | 8 |
| | D6 | 3,4-$(OMe)_2$ | F | >95 | 9.0 | 18 |
| | D7 | 3,4-$OCH_2O$ | F | >95 | 3.0 | 33 |
| Aryl-$C_3N$ | D8 | 3,4-$(OMe)_2$ | $CH_2Ph$ | 61 | | 40 |
| | D9 | 4-OMe | $CH_2Ph$ | >95 | 10 | 27 |
| | D10 | 3,4-$(OMe)_2$ | n-octyl | 65 | | 14 |
| | D11 | 4-OMe | n-octyl | 53 | | 15 |
| | D12 | 3,4-$(OMe)_2$ | H | 26 | | 11 |
| | D13 | 4-OMe | H | 46 | | 13 |
| Ring-$C_5N$ | B1 | | | 90 | 20 | 5 |

[a] two independent measurements of inhibition at 100 μM gave values of 20 and 49%

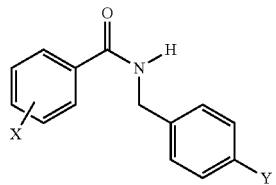

Aryl-$C_1N$ (F1-4)

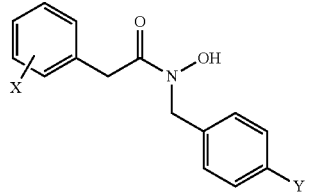

Aryl-$C_2N$ (D1-7)

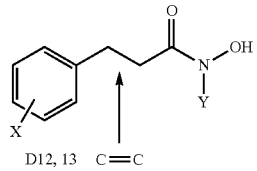

D12, 13  C≡C

Aryl-$C_3N$ (D8-13)

TABLE 1-continued

Inhibition of recombinant LeCCD1 and LeNCED1 enzymes using in vitro assays.
Enzyme assays, using *E. coli* cell extracts containing the recombinant CCD, were initially
carried out at 100 μM inhibitor concentration; for compounds showing ≥90% inhibition
of LeCCD1 at this concentration, $IC_{50}$ values were also determined. NT, not tested.
Chemical structures of hydroxamic acid inhibitors are shown below, with X and
Y given in the table. The structure of abamine is given in Fig. 3.

| Inhibitor | | | | LeCCD1a (9,10/9',10') | | LeNCED1 (11,12) |
| --- | --- | --- | --- | --- | --- | --- |
| | | | | Inhibition @ | | Inhibition @ |
| Class | Name | X | Y | 100 μM (%) | $IC_{50}$ (μM) | 100 μM (%) |

Cyclohexyl-$C_5$N (B1)

Specificity of inhibition in vitro for tomato genes LeNCED1 and LeCCD1a—In order to screen the inhibitors against enzymes which cleave carotenoids at the 9,10 position, we used the recombinant tomato LeCCD1a protein (44), because this type of enzyme can be studied using an in vitro colourimetric assay with β-apo-8'-carotenal as substrate (37). To establish the specificity of the inhibitors, they were also tested against the tomato LeNCED1 recombinant protein which cleaves 9-cis carotenoids at the 11,12 position (45). For this enzyme, the cleavage reaction was monitored by $C_{18}$ reverse phase HPLC, using 9'-cis-neoxanthin as substrate. As reported by others (46), each enzyme activity was found to be unstable (lifetime <24 h) towards storage or purification, therefore enzyme assays were carried out using recombinant cell-free extract (no cleavage activity was observed using *E. coli* extract lacking the recombinant CCD gene).

Against LeNCED1, several hydroxamic acids (notably D8, D7, and D4) showed 1.5-2 fold higher inhibitory activity than the designated NCED inhibitor, abamine (31), which in our hands showed only 20% inhibition at 100 μM concentration (see Table 1). Against LeCCD1, potent inhibition was observed by all the aryl-$C_2$N hydroxamic acids, and certain other hydroxamic acids. 4-methoxyaryl hydroxamic acids were effective inhibitors in each series, but the most potent inhibition was observed with the 4-hydroxyaryl hydroxamic acids D1, D2, and D3, which gave $IC_{50}$ values of 0.8-0.9 μM. Abamine showed only 50% inhibition of LeCCD1 at 100 μM.

Comparison of inhibition data for LeNCED1 and LeCCD1a shows that all the active compounds show some selectivity towards LeCCD1, with compounds D3, F1, and F2 showing high levels of inhibition of LeCCD1, and little or no inhibition of LeNCED1 (Table 1).

In vivo activity of inhibitors applied to *E. coli* strains expressing CCDs—Coloured *E. coli* strains that produce various carotenoids can be constructed by expression of enzymes for carotenoid synthesis (26). Upon co-expression of the appropriate CCD, the bacteria lose their colour due to cleavage of the carotenoids to colourless products (4,6,27). This technique was employed here to further explore the specificity of inhibitors, and to test their activity in vivo. The level of carotenoid in each CCD-expressing strain was compared to the level of the carotenoid in a control strain producing β-carotene but lacking any CCD gene. The difference in the carotenoid levels gave a measure of CCD activity, and inhibition of this activity was measured by addition of inhibitors to the growing medium.

The inhibitors were tested against four β-carotene-producing *E. coli* strains (supplemental Table S1). Three of the strains expressed highly divergent CCDs that cleave at the 9,10 position: AtCCD7 from *Arabidopsis* (21) and MmBCO2 from mouse (6) which both cleave at a single site (9,10 or 9',10' but not both), and the tomato enzyme LeCCD1a (44) which cleaves at both sites in the same substrate molecule (9,10/9',10' activity). The fourth strain expressed another mouse CCD, MmBCO1 (47), which cleaves centrally at 15,15'. Ourselves and other researchers (48) have found that expressing CCDs (and presumably other proteins) can lead to loss of carotenoids by non-specific means. However, detection of cleavage products by HPLC in the *E. coli* cells and media confirmed that in all four strains used here, CCD cleavage was the cause of carotenoid loss. NCED activity could not be studied in *E. coli* cells because the enzyme required for production of the 9-cis carotenoid substrates of NCED has not yet been identified. We synthesized the genes CsZCD (9) and BoLCD (49), expressed them in *E. coli*, and looked for the reported 5,6 and 7,8 cleavage activities both in vitro and in *E. coli* cells. However, we were not able to detect activity, and so it was not possible to test inhibitors against the 5,6 and 7,8 cleavage specificities.

The compounds showed different patterns of inhibition against the three 9,10 enzymes (FIG. 4). The activity of the compounds against LeCCD1a in vivo (FIG. 4) mirrored the activity observed in vitro (Table 1): D5 and D6 exhibited relatively weaker inhibition activity than the other D compounds and F3 exhibited virtually none. A different pattern was obtained with AtCCD7 in the *E. coli* system (FIG. 4), with the compounds F1 and F2, which exhibited good activity against LeCCD1a, showing poor inhibition. In contrast F1 and F2 were the most effective compounds at inhibiting MmBCO2 (FIG. 4). The 15,15' cleavage enzyme MmBCO1 was not inhibited to any significant extent by any of the compounds tested (FIG. 4).

Stimulation of shoot branching in *Arabidopsis* stem sections by application of inhibitor—Auxin inhibits the outgrowth of axillary buds in wild-type *Arabidopsis* plants. In the AtCCD7 and AtCCD8 null mutants (max3 and max4, respectively) the response to auxin is reduced, presumably due to a block in formation of an apocarotenoid hormone (recently shown (17,18) to be strigolactone or a related compound) that suppresses branching (19), and axillary buds extend earlier, leading to formation of side branches. An in vitro assay was previously developed in which the growth of axillary buds from isolated sections of Arabidopsis stem was used to assess max mutants (40). In such assays, it was reported that bud outgrowth of the max4-1 mutant (AtCCD8) was 2 days earlier than for wild-type (20) and a similar phenotype is expected of the highly branched max3-9 mutant (21). We tested hydroxamic acid inhibitors at 100 µM in this assay and found that D1 to D6, and F3 all significantly (P<0.05) advanced the timing of bud outgrowth in wild-type, with the advancement ranging from one day (D1) to three days (D3) (FIG. 5). This earlier bud outgrowth was equivalent to that observed in the AtCCD7 null mutant max3-9 (FIG. 5), and indicates an inhibition of AtCCD7 and/or possibly AtCCD8 in this tissue. The effect of the inhibitors in this assay only partially mirrored the activities in the E. coli assay, with compounds F1 and F2 having a relatively small activity in both the bud outgrowth assay (FIG. 5) and the E. coli AtCCD7 assay (FIG. 4). However, in the case of F3 there was disagreement because it was inactive in the E. coli assay for AtCCD7, but it was active in stimulating bud outgrowth. One possibility in this case is that F3 stimulated branching by inhibiting AtCCD8 (not tested in vitro or in E. coli) rather than AtCCD7.

Figure 6:
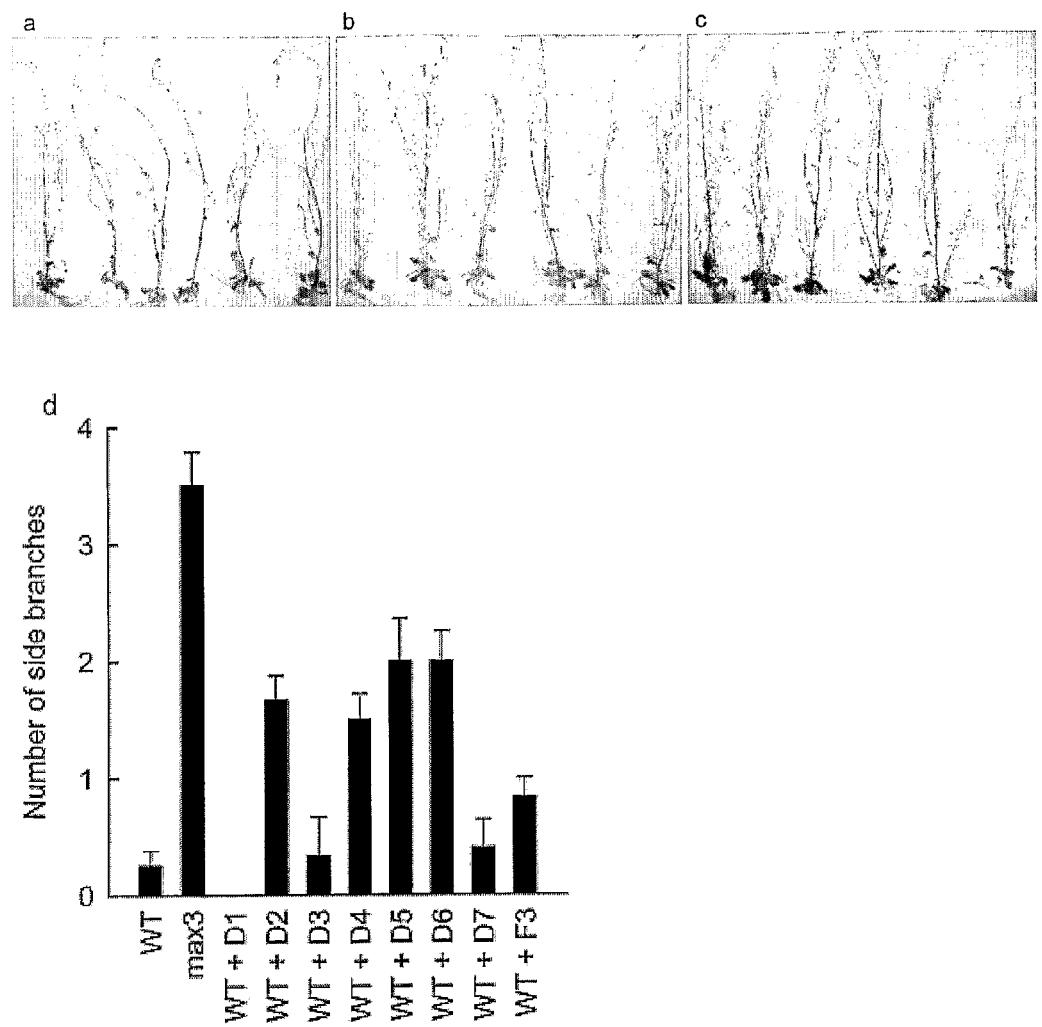
Figure 7:
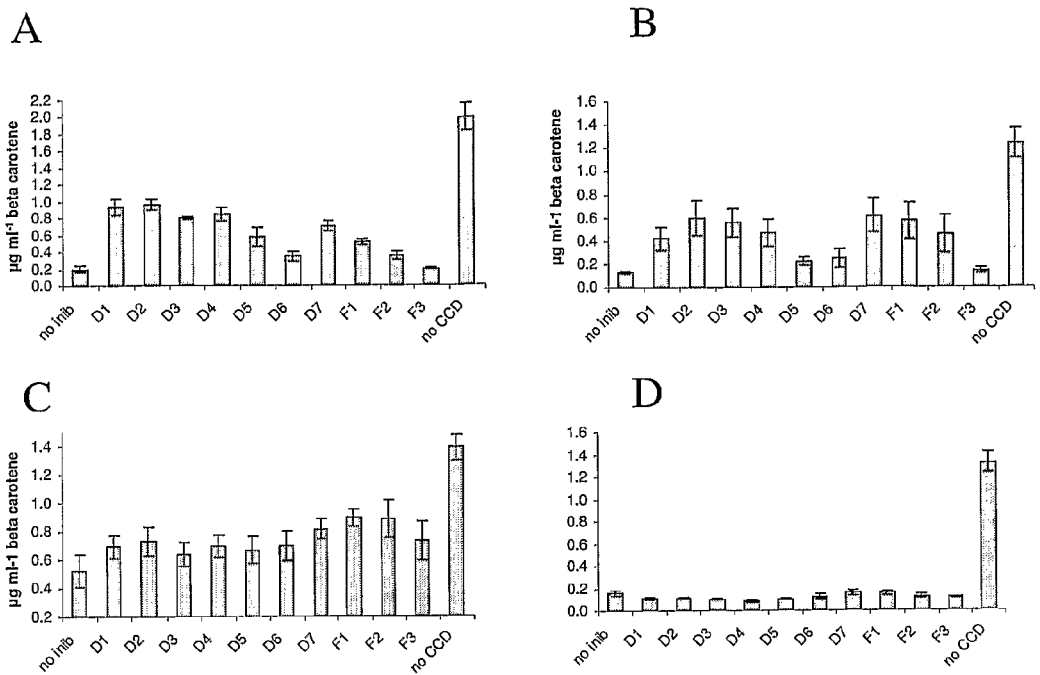

Stimulation of shoot branching in whole Arabidopsis plants—Inhibitors were also applied to Arabidopsis whole plants grown under sterile conditions in agar. The max3-9 plants (FIG. 6b) and those treated with D2, D4, D5 and D6 (FIG. 6c shows D6 treated plants) exhibited a bushy appearance compared to the untreated wild-type controls (FIG. 6a). This bushy appearance was due to the increased number of side branches from the rosette nodes, with max3-9 plants exhibiting 3 to 4 side branches compared to a mean of 0.25 for wild type. Inhibitor treated plants were intermediate (mean of approximately 2 branches) and so partially mimicked max3-9 (FIG. 6d).

The phytohormone abscisic acid (ABA) promotes dormancy in many plant structures including seeds [Finch-Savage, W. E. and G. Leubner-Metzger, *Seed dormancy and the control of germination*. New Phytologist, 2006. 171(3): p. 501-523], tuber [Suttle, J. C., *Physiological regulation of potato tuber dormancy*. American Journal of Potato Research, 2004. 81(4): p. 253-262], bulbs [Chope, G. A., L. A. Terry, and P. J. White, *Effect of controlled atmosphere storage on abscisic acid concentration and other biochemical attributes of onion bulbs*. Postharvest Biology and Technology, 2006. 39(3): p. 233-242] and buds [Le Bris, M., et al., *Regulation of bud dormancy by manipulation of ABA in isolated buds of Rosa hybrida cultured in vitro*. Australian Journal of Plant Physiology, 1999. 26(3): p. 273-281]. 9-cis-epoxycarotenoid dioxygenase (NCED) is a key rate limiting step in ABA biosynthesis [Thompson, A. J., et al., *Ectopic expression of a tomato 9-cis-epoxycarotenoid dioxygenase gene causes over-production of abscisic acid*. Plant Journal, 2000. 23(3): p. 363-74.5].

Table 1 shows that many of the hydroxamic acid compounds show some inhibitory activity against NCED in vitro, and the compounds D4, D7 and D8 have the greatest inhibition of NCED in vitro.

Figure 9:
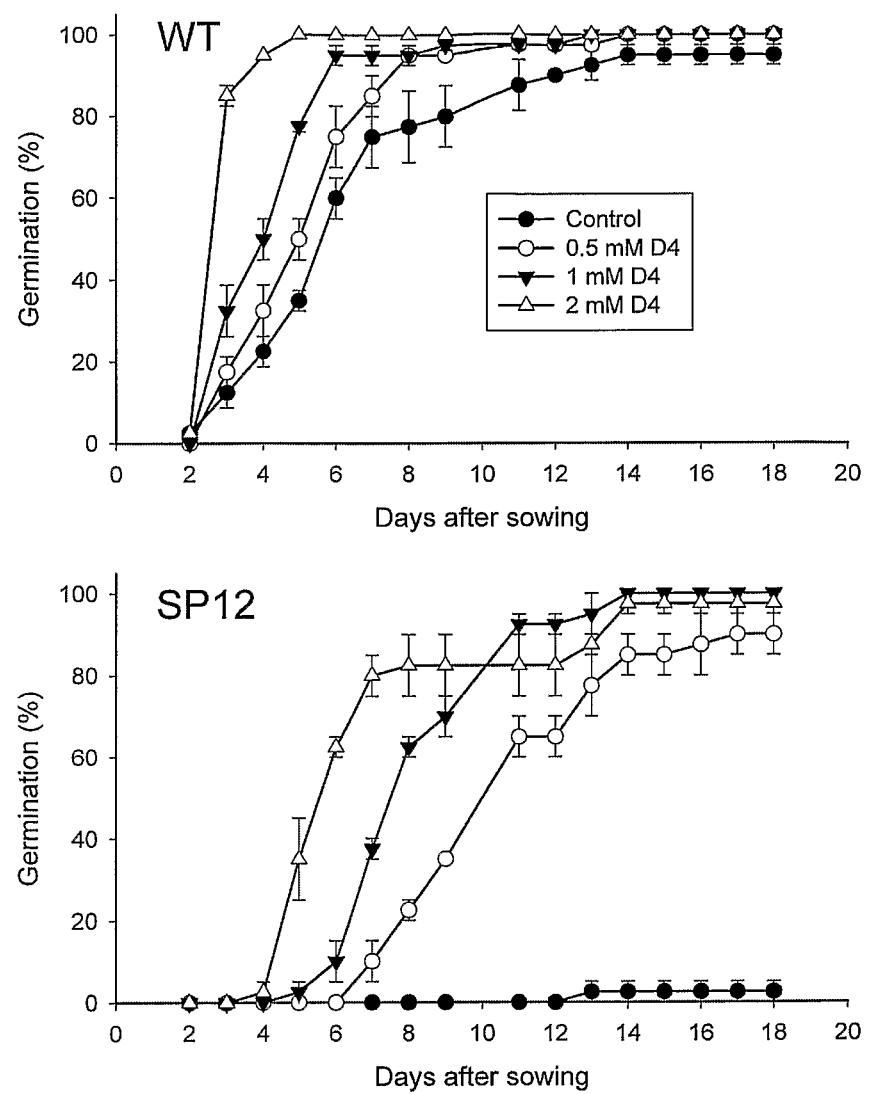

Transgenic SP12 tomato seeds we created by the inventors; these seeds have high levels of ABA and increased dormancy [Thompson, A. J., et al., *Ectopic expression of a tomato 9-cis-epoxycarotenoid dioxygenase gene causes over-production of abscisic acid*. Plant Journal, 2000. 23(3): p. 363-74 and Thompson, A. J., et al., *Regulation and manipulation of ABA biosynthesis in roots*. Plant Cell and Environment, 2007. 30: p. 67-78]. We used this seed as an assay system (addition of NCED inhibitors should promote germination) to test compounds D1 to D7 and found that D4 and D7 were the most active compounds in stimulating germination. Compound D4 promoted germination of SP12 seeds (FIG. 8) in a dose-dependent manner (FIG. 9). We also applied D4 to wild-type tomato seeds (cv. Ailsa Craig), and found that germination of these seeds was also promoted (FIG. 9) in a dose-dependent manner. Normal plant development was observed following application of D4 to wild-type or SP12 seeds when concentrations were <1 mM. Some delay in development was evident at 2 mM D4.

The commercial herbicides norflurazon and fluridone block phytoene desaturase and so block ABA biosynthesis by blocking all carotenoid synthesis (ABA is derived from carotenoids). Norflurazon and fluridone are not used commercially to release plants tissue from dormancy because blocking of carotenoid synthesis is lethal (hence their use as pre-emergent herbicides, to promote germination of seeds, and then kill the emerged seedlings by bleaching). Norflurazon pyrazinone herbicides and fluridone pyridene are not supported by the pesticide industry in Europe, and in any case both were on the banned pesticides list (July 2003), and could not now be registered in Europe.

Supplemental Data

Spectroscopic Data for Synthetic Inhibitors

D1. N-benzyl-4-hydroxyphenylacetyl hydroxamic acid. Yield 0.59 g (coupling 54%, deprotection 74%). $\delta_H$ (400 MHz, CD$_3$OD) 3.77 (2H, s, C$\underline{H}_2$CO), 4.78 (2H, s, C$\underline{H}_2$N), 6.77 (2H, d, J=8.0 Hz), 7.13 (2H, d, J=8.0 Hz), 7.25-7.35 (5H, m). $\delta_C$ (100 MHz, CD$_3$OD) 39.2, 53.1, 116.3, 127.5, 128.6, 129.3, 129.5, 131.6, 137.7, 157.2, 174.7 ppm. MS (ES) 280.1 (MNa$^+$), HRMS obs. 280.0949, calc. 280.0944 for C$_{15}$H$_{15}$NO$_3$Na.

D2. N-(4-fluorobenzyl)-4-hydroxyphenylacetyl hydroxamic acid. Yield 0.12 g (coupling 93%, deprotection 55%). $\delta_H$ (400 MHz, CD$_3$OD) 3.72 (2H, s, C$\underline{H}_2$CO), 4.78 (2H, s, C$\underline{H}_2$N), 6.73 (2H, d, J=8.0 Hz), 7.06 (2H, t, J=8.0 Hz), 7.11 (2H, d, J=8.0 Hz), 7.30 (2H, m). $\delta_C$ (100 MHz, CD$_3$OD) 39.2, 52.3, 114.9, 116.0, 116.2, 128.5, 129.5, 131.3, 131.5, 142.4 (carbonyl not seen) ppm. MS (ES) 298.1 (MNa$^+$), HRMS obs. 298.0860, calc. 298.0850 for C$_{15}$H$_{14}$NO$_3$Na.

D3. N-(4-fluorobenzyl)-3,4-dihydroxyphenylacetyl hydroxamic acid. Yield 0.08 g (coupling 50%, deprotection 78%). $\delta_H$ (300 MHz, CD$_3$OD) 3.68 (2H, s, C$\underline{H}_2$CO), 4.74 (2H, s, C$\underline{H}_2$N), 6.60 (1H, dd, J=2.0,8.0 Hz), 6.72 (1H, d, J=8.0 Hz), 6.78 (1H, d, J=2.0 Hz), 7.03 (2H, t, J=8.0 Hz), 7.28 (2H, m). $\delta_C$ (75 MHz, CD$_3$OD) 39.4, 52.3, 116.0, 116.3, 117.7, 121.9, 127.9, 131.3, 145.1, 146.2, 162.1, 165.3, 174.1 ppm. MS (ES) 314.3 (MNa$^+$).

D4. N-(4-fluorobenzyl)-4-methoxyphenylacetyl hydroxamic acid. Yield 0.24 g (coupling 78%, deprotection 83%). $\delta_H$ (400 MHz, CDCl$_3$) 3.70 (2H, s, C$\underline{H}_2$CO), 3.73 (3H, s, C$\underline{H}_3$O) 4.69 (2H, s, C$\underline{H}_2$N), 6.77 (2H, d, J=8.0 Hz), 6.94 (2H, t, J=8.0 Hz), 7.13 (2H, d, J=8.0 Hz), 7.20 (2H, m). $\delta_C$ (100 MHz, CDCl$_3$) 38.9, 40.4, 52.0, 114.5, 115.7, 115.9, 128.2, 131.1, 131.3, 159.3, 163.7 (carbonyl not seen) ppm. MS (ES) 312.2 (MNa$^+$), HRMS obs. 312.1004, calc. 312.1006 for C$_{16}$H$_{16}$NO$_3$FNa.

D5. N-benzyl-3,4-dimethoxyphenylacetyl hydroxamic acid. Yield 0.23 g (coupling 62%, deprotection 66%). $\delta_H$ (300 MHz, CDCl$_3$) 3.64 (2H, s, C$\underline{H}_2$CO), 3.70 (3H, s, OC$\underline{H}_3$), 3.76 (3H, s, OC$\underline{H}_3$), 4.65 (2H, s, C$\underline{H}_2$N), 6.63-6.73 (3H, m), 7.15-7.30 (5H, m). $\delta_C$ (75 MHz, CDCl$_3$) 38.0, 51.4, 55.1, 55.2, 110.5, 111.9, 121.0, 126.9, 127.1, 127.8, 128.3, 135.4, 147.1, 148.1, 172.1 ppm. MS (ES) 324.2 (MNa⁺), HRMS obs. 324.1216, calc. 324.1206 for $C_{17}H_{19}NO_4Na$.

D6. N-(4-fluorobenzyl)-3,4-dimethoxyphenylacetyl hydroxamic acid. Yield 0.22 g (coupling 100%, deprotection 69%). $\delta_H$ (400 MHz, CD₃OD) 3.40 (2H, s, C$\underline{H}_2$CO), 3.80 (3H, s, OC$\underline{H}_3$), 3.84 (3H, s, OC$\underline{H}_3$), 4.76 (211, s, C$\underline{H}_2$N), 6.81 (1H, d, J=8.0 Hz), 6.89 (1H, d, J=8.0 Hz), 6.91 (1H, s), 7.04 (2H, t, J=8.0 Hz), 7.30 (2H, m). $\delta_C$ (100 MHz, CD₃OD) 39.5, 52.3, 56.4, 56.6, 113.1, 114.4, 116.3, 123.0, 129.4, 131.5, 133.9, 149.4, 162.5, 164.9, 174.3 ppm. MS (ES) 342.2 (MNa⁺), HRMS obs. 342.1110, calc. 342.1112 for $C_{17}H_{18}NO_4FNa$.

D7. N-(4-fluorobenzyl)-3,4-methylenoxyphenylacetyl hydroxamic acid. Yield 0.26 g (coupling 51%, deprotection 100%). $\delta_H$ (400 MHz, CD₃OD) 3.45 (2H, s, C$\underline{H}_2$CO), 4.86 (2H, s, C$\underline{H}_2$N), 6.05 (2H, s, OC$\underline{H}_2$O), 6.85 (2H, s), 6.91 (1H, s), 7.08 (2H, t, J=8.0 Hz), 7.33 (2H, m). $\delta_C$ (100 MHz, CD₃OD) 39.7, 52.5, 102.4, 109.2, 111.0, 116.3, 123.7, 130.3, 131.5, 133.6, 149.7, 162.7, 165.1, 175.0 ppm. MS (ES) 304.1 (MH⁺), HRMS obs. 304.0980, calc. 304.0980 for $C_{16}H_{15}NO_4F$.

D8. N-benzyl-3,4-dimethoxyphenylpropionyl hydroxamic acid. Yield 0.15 g (coupling 71%, deprotection 94%). $\delta_H$ (400 MHz, CDCl₃) 2.60 (4H, m), 3.73 (6H, s, 2×OC$\underline{H}_3$), 4.68 (2H, s, C$\underline{H}_2$N), 6.63-6.73 (3H, m), 7.15-7.30 (5H, m). $\delta_C$ (100 MHz, CDCl₃) 30.4, 34.3, 51.9, 55.8, 55.9, 111.3, 111.9, 120.3, 126.9, 128.0, 128.8, 133.9, 136.2, 147.3, 148.8 (carbonyl not seen) ppm. MS (ES) 316.2 (MH⁺), HRMS obs. 316.1547, calc. 316.1549 for $C_{18}H_{21}NO_4$.

D9. N-benzyl-4-methoxyphenylpropionyl hydroxamic acid. Yield 0.13 g (coupling 82%, deprotection 82%). $\delta_H$ (400 MHz, CDCl₃) 2.82 (4H, m), 3.68 (3H, s, OC$\underline{H}_3$), 4.68 (2H, s, C$\underline{H}_2$N), 6.67 (2H, d, J=8.0 Hz), 7.01 (2H, d, J=8.0 Hz), 7.15-7.30 (5H, m). $\delta_C$ (100 MHz, CDCl₃) 28.0, 32.3, 50.9, 54.2, 112.9, 120.3, 126.6, 127.5, 128.3, 134.3, 136.3, 147.5 (carbonyl not seen) ppm. MS (ES) 286.2 (MH⁺), HRMS obs. 286.1447, calc. 286.1443 for $C_{17}H_{19}NO_3$.

D10. N-octyl-3,4-dimethoxyphenylpropionyl hydroxamic acid. Yield 0.10 g (coupling 57%, deprotection 85%). $\delta_H$ (400 MHz, CDCl₃) 0.88 (3H, t, J=7.0 Hz), 1.25-1.35 (12H, m), 2.61 (2H, t, J=7.0 Hz), 2.89 (2H, t, J=7.0 Hz), 3.39 (2H, t, J=7.0 Hz, C$\underline{H}_2$N), 3.88 (6H, s, 2×OC$\underline{H}_3$), 6.63-6.73 (3H, m), 7.15-7.30 (5H, m). $\delta_C$ (100 MHz, CDCl₃) 14.5, 23.0, 26.9, 28.0, 29.6, 31.0, 31.4, 32.2, 32.3, 36.4, 56.2, 56.3, 111.6, 112.1, 120.6, 133.4, 148.0, 149.3 (carbonyl not seen) ppm. MS (ES) 338.2 (MH⁺), HRMS obs. 337.2262, calc. 337.2253 for $C_{19}H_{31}NO_4$.

D11. N-octyl-4-methoxyphenylpropionyl hydroxamic acid. Yield 0.12 g (coupling 62%, deprotection 92%). $\delta_H$ (400 MHz, CDCl₃) 0.78 (3H, t, J=7.0 Hz), 1.20-1.35 (12H, m), 2.60 (2H, t, J=7.0 Hz), 2.85 (2H, t, J=7.0 Hz), 3.53 (2H, t, J=7.0 Hz, C$\underline{H}_2$N), 3.72 (3H, s, OC$\underline{H}_3$), 6.72 (2H, d, J=8.0 Hz), 7.05 (2H, d, J=8.0 Hz). $\delta_C$ (100 MHz, CDCl₃) 13.7, 22.6, 26.8, 27.0, 29.1, 29.4, 31.3, 32.3, 32.3, 36.4, 55.1, 113.7, 129.2, 137.2, 156.7, 172.7 ppm. MS (ES) 308.2 (MH⁺), HRMS obs. 308.2237, calc. 308.2226 for $C_{18}H_{29}NO_3$.

F1. N-benzyl-4-methoxybenzoyl hydroxamic acid. Yield 55 mg (13%). $\delta_H$ (300 MHz, CDCl₃) 3.70 (3H, s, OC$\underline{H}_3$), 4.75 (2H, s, C$\underline{H}_2$N), 6.75 (2H, d, J=8.0 Hz), 7.20-7.30 (5H, m), 7.45 (2H, d, J=8.0 Hz). $\delta_C$ (100 MHz, CDCl₃) 54.9, 55.4, 113.8, 124.3, 127.5, 128.6, 129.5, 130.1, 135.6, 161.8, 168.4 ppm. MS (ES) 258.2 (MH⁺), HRMS obs. 258.1128, calc. 258.1130 for $C_{15}H_{16}NO_3$.

F2. N-(4-fluorobenzyl)-4-methoxybenzoyl hydroxamic acid. Yield 38 mg (coupling 50%, deprotection 60%). $\delta_H$ (300 MHz, CDCl₃) 3.80 (3H, s, OC$\underline{H}_3$), 4.75 (2H, s, C$\underline{H}_2$N), 6.80 (2H, d, J=8.0 Hz), 6.95 (2H, t, J=9.0 Hz), 7.15 (2H, m), 7.40 (2H, d, J=8.0 Hz). $\delta_C$ (100 MHz, CDCl₃) 54.5, 55.4, 113.7, 115.5, 121.3, 128.4, 129.1, 129.9, 159.9, 162.0, 169.6 ppm. MS (ES) 276.2 (MH⁺), HRMS obs. 276.1039, calc. 276.1036 for $C_{15}H_{15}NO_3F$.

F3. N-benzyl-3,4-dimethoxybenzoyl hydroxamic acid. Yield 0.23 g (53%). $\delta_H$ (300 MHz, CDCl₃) 3.65 (3H, s, OC$\underline{H}_3$), 3.85 (3H, s, OC$\underline{H}_3$), 4.80 (2H, s, C$\underline{H}_2$N), 6.80 (1H, d, J=8.0 Hz), 7.03 (1H, d, J=2.0 Hz), 7.10 (1H, dd, J=2.0, 8.0 Hz), 7.25-7.35 (5H, m). $\delta_C$ (100 MHz, CDCl₃) 55.2, 55.9, 56.0, 110.5, 111.1, 121.3, 123.9, 127.1, 128.6, 128.8, 135.6, 148.9, 151.5, 168.0 ppm. MS (ES) 288.2 (MH⁺), HRMS obs. 288.1242, calc. 288.1236 for $C_{16}H_{18}NO_4$.

F4. N-(4-fluorobenzyl)-3,4-dimethoxybenzoyl hydroxamic acid. Yield 9 mg (35%). $\delta_H$ (300 MHz, CDCl₃) 3.45 (6H, s, OC$\underline{H}_3$), 4.55 (2H, s, C$\underline{H}_2$N), 6.75 (1H, d, J=8.0 Hz), 6.95 (2H, t, J=9.0 Hz), 7.25-7.35 (4H, m). MS (ES) 306.2 (MH⁺), HRMS obs. 306.1140, calc. 306.1136 for $C_{16}H_{17}NO_4F$.

B1. (2E)-3-Methyl-5-(2,6,6-trimethyl-cylohexen-1-enyl)-penta-2,4-dienoyl hydroxamic acid. 0.09 g (62%). $\delta_H$ (400 MHz, CDCl₃) 1.02 (3H, s), 1.08 (3H, s), 1.48 (2H, m), 1.62 (2H, m), 1.71 (3H, s, E isomer), 1.78 (3H, s, Z isomer), 5.68 (1H, s, Z isomer), 5.78 (1H, s, E isomer), 6.12 (1H, d, J=15.0 Hz), 6.62 (1H, d, J=15.0 Hz). $\delta_C$ (100 MHz, CDCl₃) 13.7, 18.9, 20.8, 21.5, 28.7, 32.9, 39.3, 115.0, 116.8, 129.8, 133.7, 134.5, 135.8 (carbonyl not seen) ppm. MS (ES) 273.2 (MNa⁺).

D12. 3,4-Dimethoxyphenylpropenoyl hydroxamic acid. Yield 0.18 g (54%). $\delta_H$ (400 MHz, CDCl₃) 3.79 (6H, s, 2×OC$\underline{H}_3$), 6.25 (1H, d, J=16.0 Hz), 6.85 (1H, d, J=8.0 Hz), 7.03 (2H, m), 7.42 (1H, d, J=16.0 Hz). MS (ES) 246.1 (MNa⁺).

D13. 4-Methoxyphenylpropenoyl hydroxamic acid. Yield 1.07 g (50%). $\delta_H$ (400 MHz, CD₃OD) 3.78 (3H, s, OC$\underline{H}_3$), 6.38 (1H, d, J=16.0 Hz), 6.89 (2H, d, J=8.0 Hz), 7.48 (2H, d, J=8.0 Hz), 7.56 (1H, d, J=16.0 Hz). $\delta_C$ (100 MHz, CD₃OD) 55.9, 115.5, 118.4, 128.8, 130.8, 141.6, 145.1, 167.0 ppm. MS (ES) 194.2 (MH⁺), HRMS obs. 194.0816, calc. 194.0818 for $C_{10}H_{12}NO_3$.

E1. N-benzyl-N-(4-methoxybenzyl)-glycine methyl ester. $\delta_H$ (300 MHz, CDCl₃) 3.40 (2H, s, C$\underline{H}_2$N), 3.81 (3H, s, OC$\underline{H}_3$), 3.86 (2H, s, C$\underline{H}_2$N), 3.90 (3H, s, CO₂C$\underline{H}_3$), 6.97 (2H, d, J=8.0 Hz), 7.25-7.50 (7H, m). $\delta_C$ (75 MHz, CDCl₃) 50.7, 52.6, 54.6, 56.5, 57.0, 113.1, 126.5, 127.7, 128.3, 129.5, 130.4, 135.3, 137.6, 171.4 ppm. m/z 322.1 (MNa⁺).

Supplemental Table

TABLE S1

CCD constructs used in BL21(DE3) (pAC-BETA) E. coil strains to measure levels of inhibition

| Gene (source species) | Accession number | Position cleavage | of Vector (tag) |
|---|---|---|---|
| AtCCD7 (Arabidopsis thaliana) | NM_130064 | 9, 10 | pGEX-4t (GST) |
| LeCCD1a (Solanum lycopersicum) | AY576001 | 9, 10/9', 10' | pET30 (none) |
| MmBCO2 (Mus musculus) | AJ290392 | 9, 10 | pET30 (none) |
| MmBCO1 (Mus musculus) | AF294899 | 15, 15' | pET30 (none) |

Discussion

The Inventors have designed and tested a new class of inhibitor of the carotenoid cleavage dioxygenase family that is based on a structural mimic of the substrate that positions an iron-chelating hydroxamic acid group within the active site. Positioning was achieved by varying the distance between the hydroxamic acid and an aromatic ring so that it matched the distance within the carotenoid substrate between the proximal cyclic end-group and the cleavage site. Crystal structure of ACO, a cyanobacterial CCD, indicates that cleavage position is likely to be determined by the distance between the Fe(II) catalytic centre and the opening of the long non-polar tunnel that allows access to carotenoid substrates (11). This idea is supported by the observation that for NosCCD (from *Nostoc* sp. PCC 7120) cleavage of the monocyclic γ-carotene occurs at the 7',8' position where the proximal terminus is linear, but at the 9,10 position when the proximal terminus has a more compact cyclic end group (48); indeed it was suggested that the cyclic end group may be arrested at the entrance of the tunnel (48).

The Inventors predicted from this crystal structure, and our model for the cleavage mechanism (FIG. 3), that aryl-$C_1$N, aryl-$C_2$N and aryl-$C_3$N compounds would be selective for 7,8, 9,10 and 11,12 cleavage reactions, respectively; we tested these classes against enzymes with 9,10, 11,12 and 15,15' specificities. Certain aryl-$C_1$N compounds (F1, F2) were effective inhibitors of 9,10 but not 11,12 or 15,15' cleavages. The aryl-$C_2$N compounds were potent inhibitors of 9,10 enzymes, but also had a moderate 11,12 inhibition activity. The aryl-$C_3$N compounds were much less potent against 9,10 enzymes, and although this group contained the best 11,12 inhibitor (D8), they all still maintained a somewhat greater selectivity towards the 9,10 cleavage. In comparison, a further analogue, abamineSG, was reported to be more active against the 11,12 cleavage than the 9,10 cleavage; at 100 μM it inhibited AtNCED3 by 78% and AtCCD1 by ≤20% (32). None of the compounds tested inhibited the 15,15' enzyme, presumably because the spacing was too small. Thus we conclude that the strategy of varying the positioning of the hydroxamic acid group was only moderately successful, since some overlap existed between the classes. Nevertheless, individual compounds were identified with very high specificity to the 9,10 cleavage in vitro, e.g. $IC_{50}$ for F1 was 2.0 μM but no inhibition of LeNCED 1 was detected.

The inhibitors also exhibited different patterns of activity in *E. coli* against the three different enzymes with 9,10 cleavage activity. For example, F1 and F2 had high inhibitory activity against LeCCD1 and MmBCO2 but were relatively ineffective against AtCCD7. Such differences are not surprising since MmBCO2 shares only 17-23% amino acid identity with the two plant 9,10 enzymes (LeCCD1a and AtCCD7), which are themselves highly divergent, with only 19% identity to each other. This indicates that the variants of the hydroxamic inhibitors are able to distinguish between enzymes that have similar activities but highly divergent primary structure.

The *E. coli* system proved useful in measuring the efficacy of the inhibitors in vivo. For example, the *E. coli* assays showed F1 and F2 were poor inhibitors against AtCCD7 and this was confirmed in the *Arabidopsis* bud outgrowth assay (FIG. 5), which measures AtCCD7 and/or AtCCD8 activity. However, although D5 and D6 were poor in the *E. coli* assays they showed the largest effect on whole *Arabidopsis* plants, giving the greatest number of side branches. Also D1 and D3 appeared to be good inhibitors of the 9,10 enzymes in vitro (Table 1), in *E. coli* (FIG. 4) and in the bud outgrowth assay (FIG. 5), but D3 had negative effects on growth which confounded the branching assay in whole plants, whereas plants treated with D1 grew normally and without an increase in branching. D1 and D3 both contained a more polar hydroxyl group on the aryl ring, therefore it is possible that these compounds are more actively transported in the plant, or metabolised more rapidly.

The aryl-$C_1$N inhibitors F1 and F2, which differ only by a single fluorine, caused bleaching of leaves when applied to whole *Arabidopsis* plants. It is known that a deficiency of the photoprotective carotenoids, e.g. as caused by the application of herbicides that are inhibitors of phytoene desaturase (50), results in photooxidative breakdown of chlorophyll and therefore leaf bleaching. Further, the *Arabidopsis* variegated 3 (var3) mutant, which is reported to interact with AtCCD4 in vitro, exhibits a bleached phenotype and retardation of chloroplast development (51). The aryl-$C_1$N compounds were expected to favour inhibition of CCDs with 7,8 activity, and AtCCD4 sequence is most closely related to the 7,8 cleavage enzyme CsZCD (9), hence a possible explanation for the effect of F1 and F2 may be that they inhibited the action of the Var3/AtCCD4 complex, so giving a similar phenotype to the var3 mutant. Screening for *Arabidopsis* mutants resistant to bleaching by F1 or F2 may allow the target protein to be identified, as demonstrated for other small molecules (52).

Overall, the different activities observed in different assays suggest that factors such as uptake, metabolism, and effects on non-target processes may play a role in determining the suitability and effectiveness of the inhibitors in planta. Our results underline the importance of performing secondary screens in the biological systems where the compounds are to be used. Here we have been able to demonstrate that D2, D4, D5 and D6 appear to inhibit CCDs in all the assays tested, including in planta, without negative unintended effects on whole plants. These compounds represent useful chemical genetic agents to explore the function of CCDs in plants, animals and micro-organisms.

Using the inhibitors described here, it will now be possible to inhibit the CCD(s) involved in branching in a wide range of plant species and then look for changes in carotenoids and apocarotenoids—this could provide a powerful approach for the identification of the precursors of strigolactone, the identity of other active strigolactone-related compounds, and to the further elucidation of the biosynthetic pathway. The inhibitors could also be used to probe for functional variation in the role of strigolactone between species. Branching-promoting chemicals may have applications in horticulture where compact plant architecture is often highly desirable, e.g. in orchard crops (53).

Other biological systems where genetic manipulations are not practical include the production of saffron (9) and bixin (49) in Crocus and Bixa plants respectively, where the in vivo substrates of the CCDs involved are not clear, and also in the study of the functions of mycorradicin and strigolactone in plant interactions with mycorrhyza (54) and parasitic weeds (15), respectively. Finally, there may be pharmaceutical applications for inhibitors of BCO2 in humans because products from 9,10 carotenoid cleavage have been implicated in DNA damage and carcinogenesis (55,56).

References

1. Auldridge, M. E., McCarty, D. R., and Klee, H. J. (2006) *Curr. Opin. Plant Biol.* 9, 315-321
2. Zeevaart, J. A. D., and Creelman, R. A. (1988) *Annu. Rev. Plant Physiol. Plant Mol. Biol.* 39, 439-473
3. Schwartz, S. H., Tan, B. C., Gage, D. A., Zeevaart, J. A. D., and McCarty, D. R. (1997) *Plant Physiol.* 114, 798-798
4. von Lintig, J., and Vogt, K. (2000) *J. Biol. Chem.* 275, 11915-11920
5. Wyss, A., Wirtz, G., Woggon, W. D., Brugger, R., Wyss, M., Friedlein, A., Bachmann, H., and Hunziker, W. (2000) *Biochem. Biophys. Res. Commun.* 271, 334-336
6. Kiefer, C., Hessel, S., Lampert, J. M., Vogt, K., Lederer, M. O., Breithaupt, D. E., and von Lintig, J. (2001) *J. Biol. Chem.* 276, 14110-14116
7. Hu, K. Q., Liu, C., Ernst, H., Krinsky, N. I., Russell, R. M., and Wang, X. D. (2006) *J. Biol. Chem.* 281, 19327-19338

8. Dudareva, N., Negre, F., Nagegowda, D. A., and Orlova, I. (2006) *Crit. Rev. Plant Sci.* 25, 417-440
9. Bouvier, F., Suire, C., Mutterer, J., and Camara, B. (2003) *Plant Cell* 15, 47-62
10. Juttner, F., and Hoflacher, B. (1985) *Arch. Microbial.* 141, 337-343
11. Kloer, D. P., Ruch, S., Al-Babili, S., Beyer, P., and Schulz, G. E. (2005) *Science* 308, 267-269
12. Marasco, E. K., Vay, K., and Schmidt-Dannert, C. (2006) *J. Biol. Chem.* 281, 31583-31593
13. Eisner, T., and Meinwald, J. (1966) *Science* 53, 1341-1350
14. Fester, T., Schmidt, D., Lohse, S., Walter, M. H., Giuliano, G., Bramley, P. M., Fraser, P. D., Hause, B., and Strack, D. (2002) *Planta* 216, 148-154
15. Matusova, R., Rani, K., Verstappen, F. W. A., Franssen, M. C. R., Beale, M. H., and Bouwmeester, H. J. (2005) *Plant Physiol.* 139, 920-934
16. Akiyama, K., and Hayashi, H. (2006) *Ann. Bot.* 97, 925-931
17. Gomez-Roldan, V., Fermas, S., Brewer, P. B., Puech-Pages, V., Dun, E. A., Pilot, J.
P., Letisse, F., Matusova, R., Danoun, S., Portais, J. C., Bouwmeester, H., Becard, G., Beveridge, C. A., Rameau, C., and Rochange, S. F. (2008) *Nature* 455, 189-194
18. Umehara, M., Hanada, A., Yoshida, S., Akiyama, K., Arite, T., Takeda-Kamiya, N., Magome, H., Kamiya, Y., Shirasu, K., Yoneyama, K., Kyozuka, J., and Yamaguchi, S. (2008) *Nature* 455, 195-200
19. Ward, S. P., and Leyser, O. (2004) *Curr. Opin. Plant Biol.* 7, 73-78
20. Sorefan, K., Booker, J., Haurogne, K., Goussot, M., Bainbridge, K., Foo, E., Chatfield, S., Ward, S., Beveridge, C., Rameau, C., and Leyser, O. (2003) *Genes Dev.* 17, 1469-1474
21. Booker, J., Auldridge, M., Wills, S., McCarty, D., Klee, H., and Leyser, C. (2004) *Curr. Biol.* 14, 1232-1238
22. Schwartz, S. H., Qin, X. Q., and Loewen, M. C. (2004) *J. Biol. Chem.* 279, 46940-46945
23. Alder, A., Holdermann, I., Beyer, P., and Al-Babili, S. (2008) *Biochem. J.* BJ20080568
24. Booker, J., Sieberer, T., Wright, W., Williamson, L., Willett, B., Stirnberg, P., Turnbull, C., Srinivasan, M., Goddard, P., and Leyser, O. (2005) *Dev. Cell* 8, 443-449
25. Bennett, T., Sieberer, T., Willett, B., Booker, J., Luschnig, C., and Leyser, O. (2006) *Curr. Biol.* 16, 553-563
26. Cunningham, F. X., and Gantt, E. (2007) *Photosynth. Res.* 92, 245-259
27. Schwartz, S. H., Qin, X. Q., and Zeevaart, J. A. D. (2001) *J. Biol. Chem.* 276, 25208-25211
28. Stockwell, B. R. (2000) *Nat. Rev. Genet.* 1, 116-125
29. Armstrong, J. I. (2007) *J. Sci. Food Agric.* 87, 1985-1990
30. Kaschani, F., and van der Hoorn, R. (2007) *Curr. Opin. Chem. Biol.* 11, 88-98
31. Han, S. Y., Kitahata, N., Sekimata, K., Saito, T., Kobayashi, M., Nakashima, K., Yamaguchi-Shinozaki, K., Shinozaki, K., Yoshida, S., and Asami, T. (2004) *Plant Physiol.* 135, 1574-1582
32. Kitahata, N., Han, S. Y., Noji, N., Saito, T., Kobayashi, M., Nakano, T., Kuchitsu, K., Shinozaki, K., Yoshida, S., Matsumoto, S., Tsujimoto, M., and Asami, T. (2006) *Bioorg. Med. Chem.* 14, 5555-5561
33. Suzuki, A., Akune, M., Kogiso, M., Imagama, Y., Osuki, K., Uchiumi, T., Higashi, S., Han, S. Y., Yoshida, S., Asami, T., and Abe, M. (2004) *Plant Cell Physiol.* 45, 914-922
34. Han, S. Y., Kitahata, N., Saito, T., Kobayashi, M., Shinozaki, K., Yoshida, S., and Asami, T. (2004) *Bioorg. Med. Chem. Lett.* 14, 3033-3036
35. Bergeron, R. J., and McManis, J. S. (1989) *Tetrahedron* 45, 4939-4944
36. Kawase, M., and Kikugawa, Y. (1979) *J Chem. Soc., Perkin. Trans.* 1, 643-645
37. Schmidt, H., Kurtzer, R., Eisenreich, W., and Schwab, W. (2006) *J. Biol. Chem.* 281, 9845-9851
38. Cunningham, F. X., Pogson, B., Sun, Z. R., McDonald, K. A., DellaPenna, D., and Gantt, E. (1996) *Plant Cell* 8, 1613-1626
39. Wilson, A. K., Pickett, F. B., Turner, J. C., and Estelle, M. (1990) *Mol. Gen. Genet.* 222, 377-383
40. Chatfield, S. P., Stirnberg, P., Forde, B. G., and Leyser, O. (2000) *Plant J.* 24, 159-169
41. Taylor, I. B., Sonneveld, T., Bugg, T. D. H., and Thompson, A. J. (2005) *J. Plant Growth Regul.* 24, 253-273
42. Borowski, T., Blgomberg, M. R. A., and Siegbahn, P. E. M. (2008) *Chem. Eur. J.* 14, 2264-2276
43. Kontogiorgis, C. A., Papaioannou, P., and Hadjipavlou-Litina, D. J. (2005) *Curr. Med. Chem.* 12, 339-355
44. Simkin, A. J., Schwartz, S. H., Auldridge, M., Taylor, M. G., and Klee, H. J. (2004) *Plant J.* 40, 882-892
45. Burbidge, A., Grieve, T. M., Jackson, A., Thompson, A., McCarty, D. R., and Taylor, I. B. (1999) *Plant J.* 17, 427-431
46. Vogel, J. T., Tan, B. C., McCarty, D. R., and Klee, H. J. (2008) *J. Biol. Chem.* 283, 11364-11373
47. Paik, J., During, A., Harrison, E. H., Mendelsohn, C. L., Lai, K., and Blaner, W. S. (2001) *J. Biol. Chem.* 276, 32160-32168
48. Scherzinger, D., and Al-Babili, S. (2008) *Mol. Microbiol.* 69, 231-244
49. Bouvier, F., Dogbo, O., and Camara, B. (2003) *Science* 300, 2089-2091
50. Sandmann, G., Schmidt, A., Linden, H., and Boger, P. (1991) *Weed Sci.* 39, 474-479
51. Naested, H., Holm, A., Jenkins, T., Nielsen, H. B., Harris, C. A., Beale, M. H., Andersen, M., Mant, A., Scheller, H., Camara, B., Mattsson, O., and Mundy, J. (2004) *J. Cell Sci.* 117, 4807-4818
52. Walsh, T. A., Bauer, T., Neal, R., Merlo, A. O., Schmitzer, P. R., Hicks, G. R., Honma, M., Matsumura, W., Wolff, K., and Davies, J. P. (2007) *Plant Physiol.* 144, 1292-1304
53. Quinlan, J. D., and Tobutt, K. R. (1990) *Hortscience* 25, 60-64
54. Walter, M. H., Floss, D. S., Hans, J., Fester, T., and Strack, D. (2007) *Phytochemistry* 68, 130-138
55. Yeh, S. L., and Wu, S. H. (2006) *Chem-Biol. Interact.* 163, 199-206
56. Alija, A. J., Bresgen, N., Sommerburg, O., LanghanS, C. D., Siems, W., and Eckl, P. M. (2006) *Carcinogenesis* 27, 1128-1133

Footnotes

*This work was supported by the UK Biological and Biotechnological Sciences Research Council, SCIBS initiative (Project BB/D005787).

1. Abbreviations used are: CCD, carotenoid cleavage dioxygenase; NCED, 9-cis-epoxycarotenoid dioxygenase; max, more axillary growth; $IC_{50}$, inhibitory concentration that gives 50% inhibition; WT, wild type; GST, glutathione S-transferase; PBS, phosphate buffered saline; HPLC, high performance liquid chromatography; IPTG, isopropyl β-D-1-thiogalactopyranoside; NAA, α-naphthalene acetic acid; ACO, apocarotenoid-15,15'-oxygenase.

The invention claimed is:

1. A method of stimulating germination in plant seeds and/or releasing plant tissue or plant organs from dormancy, comprising applying to a seed, plant, plant organ or plant tissue a compound of formula I:

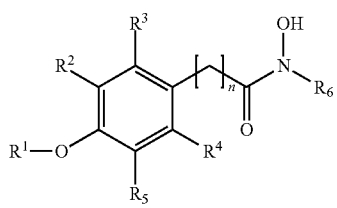

where:
$R^1$ is alkyl or H;
$R^2$, $R^3$, $R^4$ and $R_5$ are independently selectable from H, —OH, or —Oalkyl; and/or $R^1$ and $R_5$ are joined as —O(CH$_2$)$_m$—, where m is 1, 2, 3 or 4;
$R_6$ is a substituted or non-substituted alkyl, and/or substituted or non-substituted aryl; and n is an integer of 1 to 4.

2. The method according to claim 1, wherein $R_2$, $R_3$, $R_4$ and $R_5$ are H.

3. The method according to claim 1, wherein $R^1$ is a $C_1$-$C_4$ alkyl.

4. The method according to claim 1, wherein the alkyl in $R_6$ is a $C_1$-$C_{12}$ alkyl.

5. The method according to claim 1, wherein $R_6$ is a substituted alkyl or substituted aryl, substituted with one or more of halide, —OH, —NO$_2$ or —SO$_2$R'.

6. The method according to claim 1, wherein $R_6$ is a substituted or non-substituted aryl of formula —(CH$_2$)$_P$ aryl, where p is an integer of 0 to 4.

7. The method according to claim 6, wherein $R_6$ has the formula II

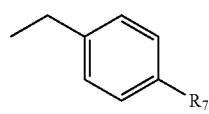

wherein $R_7$ is H, —OH, —NO$_2$, —SO$_2$R', or halide, and R' is alkyl or aminoalkyl.

8. The method according to claim 1, wherein $R^1$=Me; $R^2$, $R^3$, $R^4$ and $R_5$ are H; n=1; and $R_6$ has the formula II:

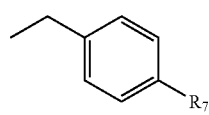

wherein $R_7$ is H, —OH, —NO$_2$, —SO$_2$R', or halide, and R' is alkyl or aminoalkyl.

9. The method according to claim 1 comprising applying the compound to one or more seeds, prior to sowing.

10. The method according to claim 1, wherein the seeds are sown into a growing medium and the compound is contacted with the seed in the growing medium.

11. The method according to claim 1, wherein the seeds are weed seeds and the weed seeds are contacted with the compound to encourage the weed seeds to germinate to produce germinated weeds, prior to the step of subsequently applying a herbicide to the germinated weeds, or carrying out tillage on the germinated weeds.

12. The method according to claim 1 wherein the compound is contacted with a tuber, corn or bulb to stimulate growth of the tuber, corn or bulb.

13. The method according to claim 1, comprising applying the compound to a plant tissue, plant organ or plant to release one or more plant tissues from dormancy.

14. The method according to claim 13, wherein the method encourages fruiting and/or flowering.

15. The plant treatment composition comprising a compound of formula I:

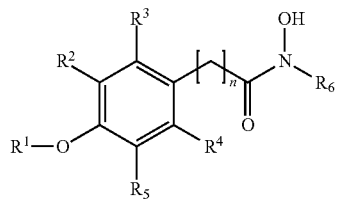

where:
$R^1$ is alkyl or H;
$R^2$, $R^3$, $R^4$ and $R_5$ are independently selectable from H, halide, —NO$_2$, —SO$_2$R', —OH, —Oalkyl where R' is alkyl or aminoalkyl; and/or $R^1$ and $R_5$ are joined as —O(CH$_2$)$_m$—, where m is 1, 2, 3 or 4;
$R_6$ has the formula II:

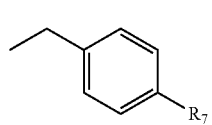

wherein $R_7$ is H, —OH, —NO$_2$, —SO$_2$R', or halide, and R' is alkyl or aminoalkyl; and n is an integer of 1 to 4.

16. The plant treatment composition according to claim 15, additionally comprising one or more adjuvants.

17. A seed coating composition comprising a composition according to claim 15 and one or more encapsulation agents or film agents.

18. A plant tissue and/or plant treated with a composition according to claim 15.

19. A seed, tuber, corn or bulb coated with a composition to claim 15.

20. An isolated compound of formula I

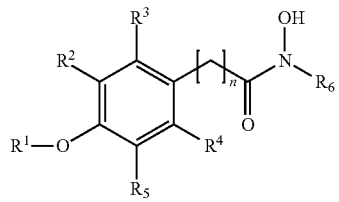

where:

$R^1$ is alkyl or H;

$R^2$, $R^3$, $R^4$ and $R_5$ are independently selectable from H, halide, $-NO_2$, $-SO_2R'$, $-OH$, $-Oalkyl$ where R' is alkyl or aminoalkyl; and/or $R^1$ and $R_5$ are joined as $-O(CH_2)_m-$, where m is 1, 2, 3 or 4;

$R_6$ has the formula II:

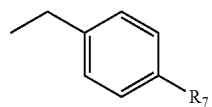

II wherein $R_7$ is H, $-OH$, $-NO_2$, $-SO_2R'$, or halide, and R' is alkyl or aminoalkyl; and n is an integer of 1 to 4.

21. The compound according to claim 20, wherein $R^1$=Me; $R^2$, $R^3$, $R^4$ and $R_5$ are H; n=1; and $R_6$ has the formula II:

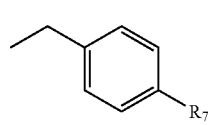

II wherein $R_7$ is H, $-OH$, $-NO_2$, $-SO_2R'$, or halide, and R' is alkyl or aminoalkyl.

* * * * *